US010930382B2

(12) United States Patent
Bengtsson et al.

(10) Patent No.: US 10,930,382 B2
(45) Date of Patent: Feb. 23, 2021

(54) SYSTEMS AND METHODS FOR ANALYSIS OF INSULIN REGIMEN ADHERENCE DATA

(71) Applicant: Novo Nordisk A/S, Bagsvaerd (DK)

(72) Inventors: Henrik Bengtsson, Taastrup (DK); Tinna Bjoerk Aradottir, Copenhagen (DK); Pete Brockmeier, Copenhagen V (DK)

(73) Assignee: Novo Nordisk A/S, Bagsvaerd (DK)

( * ) Notice: Subject to any disclaimer, the term of this patent is extended or adjusted under 35 U.S.C. 154(b) by 250 days.

(21) Appl. No.: 16/309,251

(22) PCT Filed: Jun. 22, 2017

(86) PCT No.: PCT/EP2017/065383
§ 371 (c)(1),
(2) Date: Dec. 12, 2018

(87) PCT Pub. No.: WO2018/001854
PCT Pub. Date: Jan. 4, 2018

(65) Prior Publication Data
US 2019/0156930 A1 May 23, 2019

(30) Foreign Application Priority Data
Jun. 30, 2016 (EP) .................................. 16177082

(51) Int. Cl.
G16H 20/10 (2018.01)
A61B 5/145 (2006.01)
(Continued)

(52) U.S. Cl.
CPC ........... G16H 20/10 (2018.01); A61B 5/0004 (2013.01); A61B 5/14532 (2013.01);
(Continued)

(58) Field of Classification Search
CPC ................................................ G06Q 50/22–24
See application file for complete search history.

(56) References Cited

U.S. PATENT DOCUMENTS

2011/0178820 A1* 7/2011 Soni ..................... A61B 5/0002
705/3
2014/0019396 A1 1/2014 Carlsgaard et al.
(Continued)

FOREIGN PATENT DOCUMENTS

EP 2568402 A1 3/2013
WO 2010149388 A2 12/2010
(Continued)

OTHER PUBLICATIONS

Anderson RT et al Self-reported compliance with insulin injection therapy in subjects with type 1 and 2 diabetes. 18th Congress of the International Diabetes Federation. Diabetologia. 2003;46(Suppl 2):A 275; Abstract 795.
(Continued)

Primary Examiner — Neal Sereboff
(74) Attorney, Agent, or Firm — Wesley Nicolas

(57) ABSTRACT

Systems and methods are provided for monitoring adherence to an insulin medicament dosage regimen for a subject. A data set comprising a plurality of metabolic events the subject engaged in within a period of time is obtained. Each respective metabolic event comprises a timestamp of the event and a characterization that is one of insulin regimen adherent and insulin regimen nonadherent. A plurality of primary adherence values is calculated, each respective adherence value representing a corresponding time window in a plurality of time windows within the period of time. Each time window is of a same first fixed duration. Each respective adherence value is computed by dividing a number of insulin regimen adherent events by a total number of events that have timestamps in the time window correspond- (Continued)

ing to the respective adherence value. The adherence values across the period of time are communicated thereby monitoring adherence to the insulin regimen.

14 Claims, 17 Drawing Sheets

(51) Int. Cl.
*A61B 5/00* (2006.01)
*G16H 50/20* (2018.01)
*G06F 19/00* (2018.01)
*G16H 40/63* (2018.01)

(52) U.S. Cl.
CPC .......... *A61B 5/4833* (2013.01); *A61B 5/4839* (2013.01); *A61B 5/4866* (2013.01); *A61B 5/7282* (2013.01); *A61B 5/742* (2013.01); *G06F 19/3456* (2013.01); *G06F 19/3468* (2013.01); *G16H 40/63* (2018.01); *G16H 50/20* (2018.01)

(56) References Cited

U.S. PATENT DOCUMENTS

| | | | |
|---|---|---|---|
| 2014/0172455 A1 | 6/2014 | Deng et al. | |
| 2015/0006462 A1 | 1/2015 | Sudharsan | |
| 2018/0168448 A1* | 6/2018 | Bousamra | G16H 40/67 |

FOREIGN PATENT DOCUMENTS

| | | |
|---|---|---|
| WO | 2011082212 A1 | 7/2011 |
| WO | 2012152628 A1 | 11/2012 |
| WO | 2012153295 A2 | 11/2012 |
| WO | 2012156323 A1 | 11/2012 |
| WO | 2014037365 A1 | 3/2014 |

OTHER PUBLICATIONS

Burdick J, et al Missed insulin meal boluses and elevated hemoglobin A1c levels in children receiving insulin pump therapy. Pediatrics. Mar. 2004;113 Issue 3 :e221-4.

Randloev and Poulsen. How Much Do Forgotten Insulin Injections Matter to Hemoglobin A1c in People with Diabetes? A Simulation Study. Journal of Diabetes Science and Technology; Mar. 2008 vol. 2 No. 2 pp. 229-235.

The Diabetes Control and Complications Trial Research Group. The effect of intensive treatment of diabetes on the development and progression of long-term complications in insulin-dependent diabetes mellitus. N Engl J Med. 1993 vol. 329 No. 14 pp. 977-986.

Thomas A, et al The "glucose pentagon": assessing glycemic control of patients with diabetes mellitus by a model integrating different parameters from glucose profiles. Diabetes Technology and Therapeutics; 2009 vol. 11 No. 6 pp. 399-409.

Weber et al "Visualizing Time-Series on Spirals" http://ieg.ifs.tuwien.ac.at/~aigner/teaching/ws06/infovis_ue/papers/spiralgraph_weber01visualizing.pdf Accessed Aug. 5, 2016, 6 Pages.

* cited by examiner

402 — Methods for monitoring adherence to a prescribed insulin medicament dosage regimen 206 for a subject over time using a device 250 are provided. A first data set 220 is obtained. The first data set comprises a plurality of metabolic events in which the subject engaged. The plurality of metabolic events are within a first period of time 222. Each respective metabolic event 224 in the plurality of metabolic events comprises (i) a timestamp 226 of the respective metabolic event and (ii) a first characterization 228 that is one of insulin regimen adherent and insulin regimen nonadherent.

404 — Compute a plurality of primary adherence values 230. Each respective primary adherence value 232 in the plurality of primary adherence values represents a corresponding primary time window 232 in a plurality of primary time windows within the first period of time. Each primary time window is of a same first fixed duration. Each respective primary adherence value in the plurality of primary adherence values is computed by dividing a number of insulin regimen adherent metabolic events by a total number of metabolic events in the plurality of metabolic events that have timestamps in the primary time window corresponding to the respective primary adherence value.

406 — The plurality of primary adherence values is communicated across the first period of time thereby monitoring adherence to the prescribed insulin medicament dosage regimen for the subject over time.

408 — A plurality of secondary adherence values 236 are computed. Each respective secondary adherence value in the plurality of secondary adherence values represents a corresponding secondary time window 244 in a plurality of contemporaneously overlapping secondary time windows within the first period of time. Each respective secondary adherence value in the plurality of secondary adherence values is computed by dividing a number of metabolic events that are insulin regimen adherent by a total number of metabolic events in the plurality of metabolic events that have timestamps in the secondary time window corresponding to the respective secondary adherence value. Each secondary time window in at least a subset of the secondary time windows in the plurality of secondary time windows is of longer duration than the first fixed duration. The communicating comprises communicating a superposition of the plurality of primary adherence values and the plurality of secondary adherence values across the first period of time.

410 — Each secondary time window is of a same second fixed duration that is greater than the first fixed duration.

Basal regimen: take basal dose twice per day, one in the morning and one at night time (app. 12 hours between). The characterization of a metabolic event, being a fasting event, is provided as follows:

*For every date (primary period being a day and relevant period defined by the regimen being a day):*

>  *Were two basal injections detected?*
> > *If no*
> > > *Metabolic event marked out of basal adherence, B2*
> > *If yes*
> > > *Was the time between basal injections >10 and <14 hours?*
> > > > *If yes*
> > > > > *Mark metabolic event as in basal and timing adherence, B1, C1*
> > > > *If no*
> > > > > *Mark metabolic event as in basal adherence, but out of timing adherence, B1, C1.*

Fig. 15

SYSTEMS AND METHODS FOR ANALYSIS OF INSULIN REGIMEN ADHERENCE DATA

CROSS-REFERENCE TO RELATED APPLICATIONS

This application is a 35 U.S.C. § 371 National Stage application of International Application PCT/EP2017/065383 (published as WO 2018/001854), filed Jun. 22, 2017, which claims priority to European Patent Application 16177082.1, filed Jun. 30, 2016, the contents of all above-named applications are incorporated herein by reference.

TECHNICAL FIELD

The present disclosure relates generally to systems and methods for assisting patients and health care practitioners in monitoring adherence to prescribed insulin medicament dosage regimens and for suggesting which improvements to regimen adherence will favorably affect glucose levels.

BACKGROUND

Type 2 diabetes mellitus is characterized by progressive disruption of normal physiologic insulin secretion. In healthy individuals, basal insulin secretion by pancreatic β cells occurs continuously to maintain steady glucosle levels for extended periods between meals. Also in healthy individuals, there is prandial secretion in which insulin is rapidly released in an initial first-phase spike in response to a meal, followed by prolonged insulin secretion that returns to basal levels after 2-3 hours.

Insulin is a hormone that binds to insulin receptors to lower blood glucose by facilitating cellular uptake of glucose, amino acids, and fatty acids into skeletal muscle and fat and by inhibiting the output of glucose from the liver. In normal healthy individuals, physiologic basal and prandial insulin secretions maintain euglycemia, which affects fasting plasma glucose and postprandial plasma glucose concentrations. Basal and prandial insulin secretion is impaired in Type 2 diabetes and early post-meal response is absent. To address these adverse events, patients with Type 2 diabetes are provided with insulin treatment regimens. Patients with Type 1 diabetes are also provided with insulin treatment regimens.

Some diabetic patients only need a basal insulin treatment regimen to make up for deficiencies in pancreatic β cells insulin secretion. Some patients need both basal insulin treatment and bolus insulin treatment. Thus, patients that require both basal insulin treatment and bolus insulin treatment take a periodic basal insulin medicament treatment, for instance once or twice a day, as well as one or more bolus insulin medicament treatments with meals.

The goal of these insulin treatment regimens is to achieve steady glucose levels. The success of an insulin treatment regimen in a subject can be deduced by taking continuous glucose level measurements of a subject or by measuring HbA1c levels. The term "HbA1c" refers to glycated haemoglobin. It develops when haemoglobin, a protein within red blood cells that carries oxygen throughout the body, joins with glucose in the blood, thus becoming "glycated." By measuring glycated haemoglobin (HbA1c), health care practitioners are able to get an overall picture of average glucose levels over a period of weeks/months. For people with diabetes, the higher the HbA1c, the greater the risk of developing diabetes-related complications Insulin treatment regimen nonadherence is a barrier for diabetes patients to reaching suitable HbA1c goals. Insulin regimen adherence is typically defined as the degree to which a patient correctly follows medical advice (e.g., a standing insulin regimen for a subject comprising at least a basal insulin medicament dosage regimen), but can also be, for example, consistency in diet and exercise. The reasons for nonadherence are many and different. One reason for nonadherence is poor health literacy and comprehension of treatment. Patients fail to understand glucose measurement results, lack positive feedback when adherent, or feel a lack of urgency. Another reason for nonadherence is the fear of side effects. For instance, the fear of hypoglycaemia if the patient strictly adheres to the standing insulin regimen. Yet another reason for nonadherence is the hassle and time-consuming aspect of conventional standing insulin regimens, which often entail home-logging data and frequent injections and glucose measurements. Still another reason for nonadherence is an inability to pinpoint the source of nonadherence that is the actual source of the adverse effect on stable glucose levels.

International Publication Number WO 2012/152295 A2 to Insulin Medical Ltd. optimizes insulin absorption by using one or more sensors and actuators configured to provide data relating to a user's meal status, meal timing, the timing of administered drug, drug dose, drug type, the logging of user activity, and the analysis thereof. For instance, WO 2012/152295 A2 discloses a device that may be placed over an injection site or an injection port to treat the tissue at the injection site, while collecting information on the injected drug at the time of injections with an option to provide feedback to the user, such as alerts on missed injections. WO 2012/152295 A2 further discloses using meal data and other subject data, such as the activity of the subject, to facilitate mapping the subject activity relative to injection events and optionally meal events to provide for fine control of the systemic metabolic process of glucose and insulin and therefore minimize occurrence of post prandial hyperglycemic and hypoglycemic events. However, WO 2012/152295 A2 fails to provide satisfactory ways to determine and quantify the effects of insulin regimen adherence, or lack thereof, on the health of a subject (e.g., glucose levels of the subject) or to provide guidance on what forms of insulin regimen adherence would benefit a subject. In essence, WO 2012/152295 A2 fails to provide satisfactory ways to pinpoint precisely what forms of regimen nonadherence are most adversely affecting glucose levels. Moreover, generally, WO 2012/152295 A2 fails to provide overall feedback on the subject's adherence to an insulin medicament regimen. Further, the meal detection in WO 2012/152295 A2 is not based upon autonomous glucose measurements and thus the reliability of the meal detection in WO 2012/152295 A2 is uncertain.

International Publication Number WO 2014/037365 A1 to Roche Diagnostics GMBH describes methods and apparatuses for analyzing blood glucose data and events, and, in particular, to computer implemented methods for visualizing correlations between blood glucose data and events associated with the blood glucose data such as meals. However, WO 2014/037365 A1 fails to disclose any categorization of meals in terms of insulin regimen adherence. Further, WO 2014/037365 A1 A2 fails to provide satisfactory ways in which to determine and quantify the effects of insulin regimen adherence, or lack thereof, on the health of a subject or to provide guidance on what forms of insulin regimen adherence would benefit a subject.

US Publication Number US 2015/0006462 A1 describes a system for managing a patient's medical adherence, wherein the system is adapted for performing a method comprising receiving data related to a patient, the data including information related to a prescribed medication regimen having one or more medications, patient behavior data, a respective literacy level associated with each of the one or more medications. The method further comprises calculating a compliance to dosage and a compliance to time for each of the one or more medications based on the received data. Compliance to dosage, can for example be calculated as if a patient was prescribed 10 units of a medication in a day and took only 8 units, the respective compliance to disease is obtained by dividing the amount of units actually consumed by the prescribed units. In this instance it would be 0.8. Compliance to time, can for example be calculated as follows. For ten dosages prescribed throughout the day, the Boolean values may be utilized to calculate an overall value for the day. For example, if 8 out of 10 actual consumption times for a particular medication complied with the prescribed dosage times, then the actual consumption time would be assigned a "1" for those 8 instances and a "0" would be assigned for the other two instances. Accordingly a compliance value of 0.8 may be calculated for the compliance to time for that particular medicine by dividing the overall Boolean value with the total instances. The method further comprises calculating a drug adherence count associated with each of the one or more medications by summing at least two of the compliance to dosage, compliance to time and the respective literacy level associated with each of the one or more medications. The literacy level is a metric to assess the familiarity of a patient with a prescribed regimen and its medications, and it may be impacted based on occurrence of a condition based on lack of medical adherence by a patient, e.g., effects based on user behaviour, such as lowering of blood sugar level due to missing medication. The method further comprises determining a daily medication adherence value and a daily medication adherence baseline value, and a threshold based on the ratio between the two values. The threshold can be used to determine whether an intervention is required. However, US 2015/006462 A1 fails to disclose how to automatically obtain metabolic events that are related to the prescribed insulin medicament dosage regimen, and thereby fails to systematically monitor adherence for a subject engaged in such metabolic events as a part of the daily routines. In fact US 2015/0006462 A1 suggests a generic method for any medicament, where it is assumed that the prescribed dose events are independent of the users behavior, e.g., 10 units or 10 doses are taken during a day or at prescribed times. Such a method would fail to track adherence, where the number of bolus injection events may vary due to user behavior, e.g., the user have more meals than expected. In general, US 2015/0006462 A1 does not solve the problem of how to systematically allow tracking of adherence based on well defined reference points in time, and is limited to track adherence within the boundaries specified by periods, where the beginning of the period and the end of the period is pre-defined in relation to the structure of a calendar, e.g., 10 units during a day.

A drawback of adherence algorithms based on calendar periods can be explained by considering an example for a basal insulin dosage regimen specifying 1 bolus injection per day, in combination with an adherence tracking algorithm based on a calendar day of 24 hours. The calendar day starts at midnight. On the first day of the example basal insulin is injected at 23:00 PM, on the second day basal insulin is omitted, but on the third day basal insulin is injected at 00:30 AM, and 23:00 PM. In that case an adherence algorithm based on a 24 hours calendar day would characterize day 1 as in-adherence but day 2 and 3 as nonadherent. Three injections were applied with some degree of regularity, but only 1 out of three days were categorized in adherence. Although US 2015/006462 suggests that adherence can be a function of a time delay, this functional relation is only possible, if at well defined reference time is established, as is the case in the described example where insulin is to be injected a 2 PM with an expectation of a meal to be consumed at 2:30. However, as mentioned previously user behaviour does not always follow expectations and there can be drawbacks associated with the use of expectations for reference times, and as also mentioned there can be drawbacks associated with only using calendar days to establish a measure of basal adherence.

International Publication Number WO 2010/149388 A2 to Roche Diagnostics GMBH describes a method of measuring adherence to following or achieving prescribed therapy steps to achieve stated target goals for improved chronic disease self-management. The method comprises defining a plurality of adherence units, each adherence unit containing a plurality of rules governing activities which need to be accomplished in order to complete the prescribed therapy steps; collecting data when the activities are accomplished specifying a time window of interest in the collected data; determining total number of adherence units in the collected data which fall within the specified time window of interest; counting each of the adherence units in the specified time window of interest as an adhered unit when the collected data indicates the accomplished activities were in accordance to the rules; determining adherence as a percentage of the count for the adhered units to the total number of adherence units for the specified time window; and providing at least one of the determined adherence percentage and adherence count for the specified time window. The publication further describes, a computer program, when running on a processing device, instructing the processing device to collect the data regarding an individual's activities per the prescribed (i.e., inputted and selected) protocol(s). The information regarding each activity is captured by the processing device by the computer program instructing the processing device to prompt the individual via the user interface or other suitable output hardware and to accept user inputs providing the information. The computer program then stores the inputted information in a memory of the processing device as collected data. In one embodiment, the computer program annotates the collected data regarding the protocol and/or activity, such as with a timestamp of start and completion, contextual information, and other relevant quantified and subjective data. Recording of the activity and managing the associated information via the above mentioned data collection processes enables such data to be analyzed in order to provide an assessment of an individuals adherence level. In particular, via the data collection processes, the data information and associations are captured within the memory of the processing device (or a database) such that the recorded sequence of activities has no ambiguity. The collected data is then utilized in later steps for extracting relevant subsets of data, applying adherence rules, and providing a number either as a ratio or in percentage format or an equivalent which indicates the extent to which adherence is accomplished. Even though an activity unit is generally of finite duration, the start of activity is considered as the absolute time for the activity unit 16. For example, a breakfast activity time is the time at which the breakfast activity unit is initiated. If the breakfast activity consists of a number of activity steps, such as for example, estimating carbohydrates in the breakfast meal, followed by measuring blood glucose (bG), followed by computation of insulin dose, followed by eating of the breakfast meal, followed by a 2-hour post-prandial measuring of bG, then the breakfast activity is timed as per preference or choice for marking the activity as preferably suggested by physician, so for example when the individual starts the estimation of the carbohydrate in the breakfast. As appears, WO 2010/149388 A2 relies on collecting data by prompting a user, and the collected data, therefore, comprises user input activities. WO 2010/149388 does not solve the problem of measuring adherence of a metabolic activity relevant to the prescribed regimen in situations where a user forgets to input when prompted, is unable to answer when prompted or for some reason inputs wrong data to the memory when prompted, and it does not solve the problem of directly monitoring adherence based on a metabolic activity that a user has engaged in, and not merely intends to engage in, or have engaged in a while ago. In other words the timing between user input activities and the metabolic activity relevant for monitoring adherence is subject to uncertainty. Given the above background, what is needed in the art are systems and methods that provide satisfactory ways to pinpoint what forms of regimen nonadherence are adversely affecting glucose levels in diabetic patients.

The object of the present disclosure is to provide systems and methods for reliably monitoring and communicating insulin regimen adherence and to pinpoint what forms of regimen nonadherence are adversely affecting glucose levels in diabetic patients.

SUMMARY

In the disclosure of the present invention, embodiments and aspects will be described, which will address one or more of the above objects or which will address objects apparent from the below disclosure as well as from the description of exemplary embodiments.

The present disclosure addresses the above-identified need in the art by providing methods and apparatus for assisting patients and health care practitioners in managing insulin delivery to diabetic patients. Using the systems and method of the present disclosure, patients or health care practitioners can determine what form of regimen nonadherence most adversely affects glucose levels. For instance, using the systems and methods of the present disclosure, the effect of noncompliant meals, fasting events, bolus injections, or basal injections on glucose levels is ascertained and can be used to pinpoint what forms of regimen nonadherence are adversely affecting glucose levels.

Thus, the present disclosure relates to the computation, processing, and visualization of prescribed insulin medicament dosage regimen adherence data that provides a patient and/or a health care practitioner with the ability to monitor adherence to insulin treatment and thereby the ability to pinpoint to which degree and how adherence affects the regimen treatment results.

In one aspect of the present disclosure, systems and methods are provided for monitoring adherence to an insulin medicament dosage regimen for a subject. A data set comprising a plurality of metabolic events (e.g., periods of fasting, meals, etc.) the subject engaged in within a period of time (e.g., the past week, the past two weeks, the past month, etc.) is obtained. Each respective metabolic event comprises a timestamp of the event and a characterization that is one of insulin regimen adherent and insulin regimen nonadherent. A plurality of primary adherence values is calculated. Each respective primary adherence value represents a corresponding primary time window in a plurality of primary time windows within the period of time. Each such primary time window is of a same first fixed duration (e.g. 24 hours). Each respective primary adherence value is computed by dividing a number of insulin regimen adherent events that have timestamps in the primary time window corresponding to the respective primary adherence value by a total number of events that have timestamps in the primary time window corresponding to the respective primary adherence value. The primary adherence values across the period of time are communicated (e.g., displayed on a screen, sent to a remote server, input into a regimen analysis program) thereby monitoring adherence to the insulin regimen.

Hereby is provided a system and method which establishes adherence monitoring based on metabolic events, which the subject actually engaged in, and thereby eliminates the risk of user behaviour not always follows expectations. The system and the method solves the problem of how to systematically allow tracking of adherence based on well defined reference points in time. As the data set only comprises metabolic events that the subject engaged in, the system and the method does not rely on input on a user response, and it thereby solves the problem of prior art. As the data set comprises timestamps for each metabolic event, which the subject engaged in the adherence is monitored with a high degree of uncertainty. The use of data comprising metabolic events that the subject actually engaged in for the purpose of monitoring adherence has not been previously used or described, nor has the importance of using such data in order to minimize uncertainty of the monitored adherence.

In a further aspect, the timestamp of the metabolic event is derived from autonomously timestamped measurements of an indicator of the metabolic event.

In a further aspect, the timestamp of the metabolic event is derived from autonomous timestamped glucose measurements, wherein the glucose measurements is an indicator of the metabolic event, i.e., the glucose measurement is a measurement of the glucose concentration in the blood stream.

In a further aspect, the timestamp of the metabolic event is derived from autonomous timestamped glucagon, lipids or amino acids measurements, wherein the glucagon, lipids or amino acid measurements are indicators of the metabolic event, i.e., the measurements are measurements of the concentration of the respective molecules in the blood stream.

In a further aspect, autonomous measurements are measurements obtained by a measuring device, wherein the measuring is undertaken or carried on without outside control of a user. Hereby is provided data that do not rely on input controlled by the subject or an operator of the device.

In a further aspect, autonomous measurements are measurements obtained by a device measuring at a specified or a variable frequency.

In a further aspect, the method further comprises: computing a plurality of secondary adherence values (236), wherein each respective secondary adherence value in the plurality of secondary adherence values represents a corresponding secondary time window in a plurality of contemporaneously overlapping secondary time windows within the first period of time, each respective secondary adherence value in the plurality of secondary adherence values is computed by dividing a number of metabolic events that are insulin regimen adherent by a total number of metabolic events in the plurality of metabolic events that have timestamps in the secondary time window corresponding to the respective secondary adherence value, and each secondary time window in at least a subset of the secondary time windows in the plurality of secondary time windows is of longer duration than the first fixed duration; and wherein the communicating comprises communicating a superposition of the plurality of primary adherence values and the plurality of secondary adherence values across the first period of time.

In a further aspect, the method further comprises: identifying a trend in adherence to the prescribed insulin medicament dosage regimen for the subject as a drop off in the plurality of primary adherence values or the plurality of secondary adherence values below a first threshold adherence value for at least a second threshold amount of time; and reducing amounts of insulin medicament dosage in the insulin medicament dosage regimen for the subject when the trend is identified.

In a further aspect, each metabolic event in the plurality of metabolic events is a fasting event and the insulin medicament dosage regimen is a basal insulin medicament dosage regimen.

In a further aspect, the first fixed duration is a week, and each respective secondary time window in the plurality of secondary time windows represents three months in the first time period.

In a further aspect, each metabolic event in the plurality of metabolic events is a meal event and the insulin medicament dosage regimen is a bolus insulin medicament dosage regimen.

In a further aspect, the first fixed duration is a day, and each respective secondary time window in the plurality of secondary time windows represents a running average from the beginning of the first time period.

In a further aspect, the method further comprises: obtaining an HbA1c lookup table that includes a calculated HbA1c increase as a function of adherence values in the plurality of primary adherence values; and communicating an indication of which respective primary adherence values in the plurality of primary adherence values cause the calculated HbA1c increase to be over a threshold value according to the HbA1c lookup table.

In a further aspect, each secondary time window is of a same second fixed duration that is greater than the first fixed duration.

In a further aspect, the respective metabolic events in the plurality of metabolic events that occur earlier than a set cutoff time are down-weighted relative to respective metabolic events in the plurality of metabolic events that occur after the set cutoff time in each respective primary time window.

In a further aspect, the respective metabolic events in the plurality of metabolic events are down-weighted as a linear function of time in each respective primary time window.

In a further aspect, the device is a mobile device that includes a display (282) and the communicating includes presenting the superposition on the display.

In a further aspect, the method further comprises: obtaining a second data set, the second data set comprising a plurality of autonomous glucose measurements of the subject and, for each respective autonomous glucose measurement in the plurality of autonomous glucose measurements, a glucose measurement timestamp representing when the respective measurement was made.

In a further aspect, the communicating provides the plurality of autonomous glucose measurements temporally matched to the plurality of primary adherence values over time within the first period of time.

In a further aspect, the device further comprising a wireless receiver, and wherein the second data set is obtained wirelessly from a glucose sensor affixed to the subject.

In a further aspect, the method comprises: obtaining a third data set from one or more insulin pens used by the subject to apply the insulin medicament dosage regimen, the third data set comprises a plurality of insulin medicament records, each insulin medicament record in the plurality of medicament records comprising: (i) a respective insulin medicament injection event including an amount of insulin medicament injected into the subject using a respective insulin pen in the one or more insulin pens and (ii) a corresponding electronic timestamp that is automatically generated by the respective insulin pen upon occurrence of the respective insulin medicament injection event; identifying the plurality of metabolic events using the plurality of autonomous glucose measurements of the subject and the respective timestamps in the second data set; applying a first characterization to each respective metabolic event in the plurality of metabolic events, wherein the first characterization is one of insulin regimen adherent and insulin regimen nonadherent, a respective metabolic event is deemed basal regimen adherent when the second data set includes one or more medicament records that establish, on a temporal and quantitative basis, adherence with the insulin medicament dosage regimen during the respective metabolic event, and a respective metabolic event is deemed insulin regimen nonadherent when the second data set fails to include one or more medicament records that establish, on a temporal and quantitative basis, adherence with the insulin medicament dosage regimen.

In a further aspect, the method comprises: obtaining a third data set from one or more insulin pens used by the subject to apply the insulin medicament dosage regimen, the third data set comprises a plurality of insulin medicament records, each insulin medicament record in the plurality of medicament records comprising: (i) a respective insulin medicament injection event including an amount of insulin medicament injected into the subject using a respective insulin pen in the one or more insulin pens and (ii) a corresponding electronic timestamp that is automatically generated by the respective insulin pen upon occurrence of the respective insulin medicament injection event; identifying the plurality of fasting events using the plurality of autonomous glucose measurements of the subject and the respective timestamps in the second data set; applying a first characterization to each respective fasting event in the plurality of fasting events, wherein the first characterization is one of insulin regimen adherent and insulin regimen nonadherent, a respective fasting event is deemed basal regimen adherent when the second data set includes one or more medicament records that establish, on a temporal and quantitative basis, adherence with the insulin medicament dosage regimen during the respective fasting event, and a respective fasting event is deemed insulin regimen nonadherent when the second data set fails to include one or more medicament records that establish, on a temporal and quantitative basis, adherence with the insulin medicament dosage regimen during the respective fasting event.

In a further aspect the medicament record further comprises a type of insulin medicament, and wherein, a respective fasting event is deemed insulin regimen adherent when one or more medicament records in the plurality of medicament records further indicates in the third data set, on a type of insulin medicament basis, adherence with the standing insulin medicament dosage regimen during the respective fasting event, and a respective fasting event is deemed insulin regimen nonadherent when the plurality of medicament records in the third data set further fails to indicate adherence, on a type of insulin medicament basis with the insulin medicament dosage regimen during the respective fasting period.

In a further aspect the insulin regimen adherent is defined basal regimen adherent, and insulin regiment nonadherent is defined basal regimen nonadherent.

In a further aspect, the method comprises: obtaining a third data set from one or more insulin pens used by the subject to apply the insulin medicament regimen, the third data set comprises a plurality of insulin medicament records, each insulin medicament record in the plurality of medicament records comprising: (i) a respective insulin medicament injection event including an amount of insulin medicament injected into the subject using a respective insulin pen in the one or more insulin pens and (ii) a corresponding electronic timestamp that is automatically generated by the respective insulin pen upon occurrence of the respective insulin medicament injection event; the method further comprises identifying a plurality of meal events using the plurality of autonomous glucose measurements and the corresponding timestamps in the second data set; applying a second characterization to each respective meal event in the plurality of meal events, wherein the second characterization is one of insulin regimen adherent and insulin regimen nonadherent, a respective meal event is deemed insulin regimen adherent when one or more medicament records in the plurality of medicament records indicates in the third data set, on a temporal basis, a quantitative basis, adherence with the insulin medicament dosage regimen during the respective meal, and a respective meal is deemed insulin regimen nonadherent when the plurality of medicament records in the third data set fails to indicate adherence, on a temporal basis, and a quantitative basis with the insulin medicament dosage regimen during the respective meal.

In a further aspect the medicament record further comprises a type of insulin medicament, and wherein, a respective meal event is deemed insulin regimen adherent when one or more medicament records in the plurality of medicament records further indicates in the third data set, on a type of insulin medicament basis, adherence with the insulin medicament dosage regimen during the respective meal, and a respective meal is deemed insulin regimen nonadherent when the plurality of medicament records in the third data set further fails to indicate adherence, on a type of insulin medicament basis with the insulin medicament dosage regimen during the respective meal.

In a further aspect the insulin regimen adherent is defined as bolus regimen adherent, and insulin regiment nonadherent is defined as bolus regimen nonadherent.

In a further aspect, the metabolic events are automatically obtained from measurement relating to a body function indicating a metabolic event like chewing or swallowing. Depending on the intensity chewing or swallowing may be an indication of a meal event.

In a further aspect, the metabolic events are inherently timestamped, i.e., the timestamp of the metabolic event is a direct consequence of the occurrence of the metabolic event and the timestamp is acquired in response to this occurrence.

Hereby is provided a system ensuring that adherence is monitored with respect to metabolic events that the subject has engaged in, and as the metabolic event is timestamped there is provided a well defined reference in time, allowing the characterization of adherence to utilize the timestamp.

In a further aspect, the timestamp relating to a respective metabolic event is used as a starting point for examining whether the metabolic event is insulin regimen adherent or insulin regimen nonadherent.

In a further aspect, wherein the metabolic events are fasting event, the fasting events are identified using the autonomous timestamped glucose measurements of the subject.

In a further aspect, wherein the metabolic events are meal events, the meal events are identified using the autonomous timestamped glucose measurements.

In a further aspect, metabolic events can be a metabolic event defined in the medicament regimen, which can be automatically identified from a device continuously measuring an indicator of an event relating to a metabolic state of the subject, whereby the device allows the metabolic event to be timestamped and to be characterized with respect to the medicament regimen as regimen adherent or regimen nonadherent. For example, a metabolic event defined according to the medicament regimen could be a meal event, wherein the medicament regimen determines that bolus insulin should be administered based on glucose measurements relating to this event, or it could be a fasting event, wherein the medicament regimen determines that basal insulin should be administered based on glucose measurements relating to this event.

In some embodiments the characterization of a metabolic event as insulin regimen adherent can be determined as a degree or percentage of insulin regimen adherent depending on the estimated glycemic effect of taking a dose later than recommended according to the insulin medicament dosage regimen or taking an amount of dose below or above a recommended dose.

In another aspect of the present disclosure, a computer program is provided comprising instructions that, when executed by one or more processors, perform a method comprising:

obtaining a first data set, the first data set comprising a plurality of metabolic events the subject engaged in, wherein the plurality of metabolic events are within a first period of time and each respective metabolic event in the plurality of metabolic events comprises (i) a timestamp of the respective metabolic event and (ii) a first characterization that is one of insulin regimen adherent and insulin regimen nonadherent, computing a plurality of primary adherence values, wherein each respective primary adherence value in the plurality of primary adherence values represents a corresponding primary time window in a plurality of primary time windows within the first period of time, each primary time window is of a same first fixed duration, and each respective primary adherence value in the plurality of primary adherence values is computed by dividing a number of insulin regimen adherent metabolic events that have timestamps in the primary time window corresponding to the respective primary adherence value by a total number of metabolic events in the plurality of metabolic events that have timestamps in the primary time window corresponding to the respective primary adherence value; and communicating the plurality of primary adherence values across the first period of time thereby monitoring adherence to the prescribed insulin medicament dosage regimen for the subject over time.

In a further aspect is provided a computer-readable data carrier having stored thereon the computer program.

BRIEF DESCRIPTION OF THE DRAWINGS

FIGS. 4A, 4B, and 4C collectively provide a flow chart of processes and features of a device for monitoring adherence to a prescribed insulin medicament dosage regimen for a subject over time in accordance with various embodiments of the present disclosure.

FIG. 15 illustrates an algorithm for characterizing metabolic events in accordance with an embodiment of the present disclosure.

Like reference numerals refer to corresponding parts throughout the several views of the drawings.

DETAILED DESCRIPTION

Figure 1:
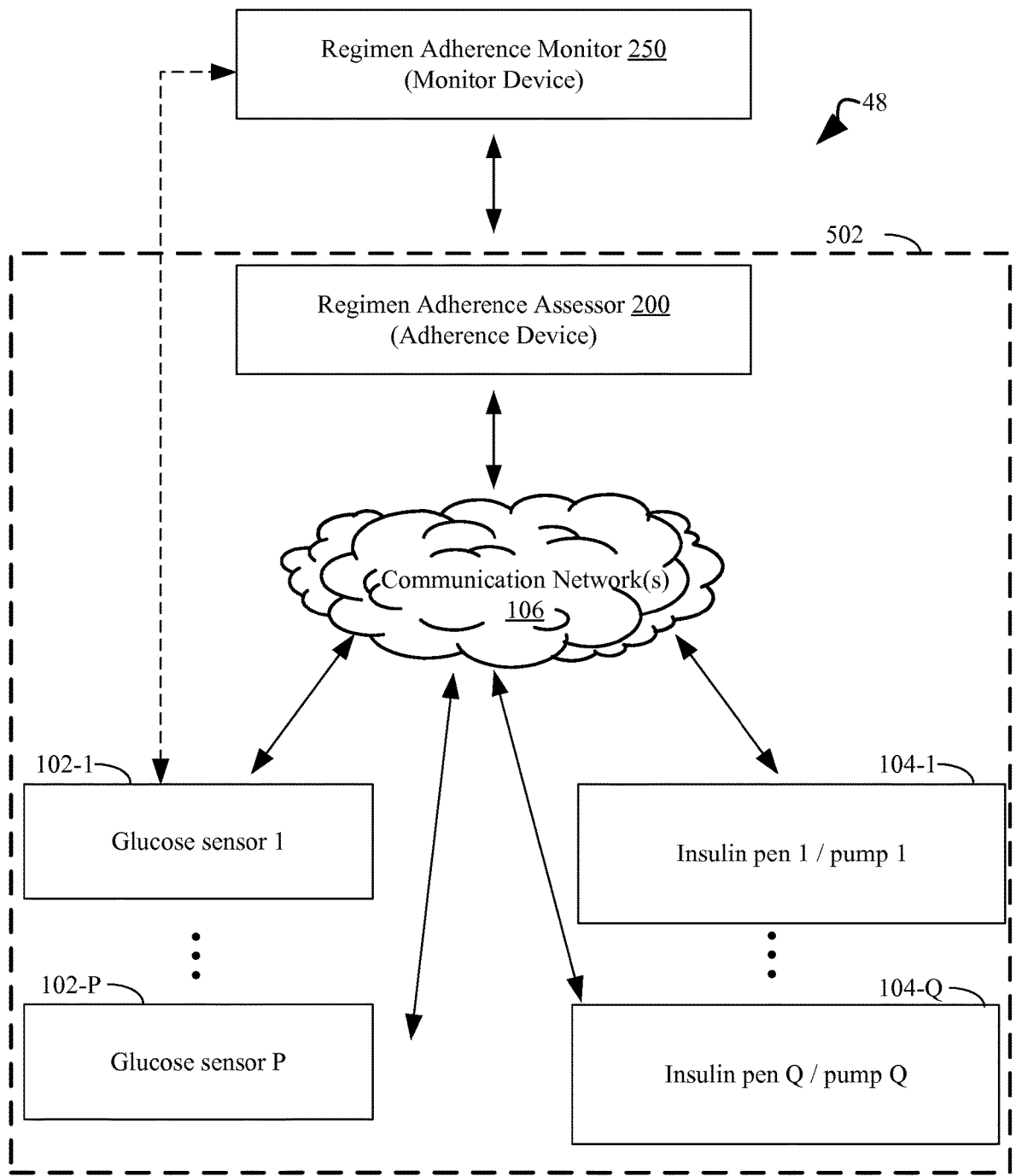
FIG. 1 illustrates an exemplary system topology that includes a regimen adherence monitor device for monitoring adherence to a prescribed insulin medicament dosage regimen for a subject over time, a regimen adherence assessor device for analyzing and preparing regimen adherence data, one or more glucose sensors that measure glucose data from the subject, and one or more insulin pens or pumps that are used by the subject to inject insulin medicaments in accordance with the prescribed insulin medicament dosage regimen, where the above-identified components are interconnected, optionally through a communications network, in accordance with an embodiment of the present disclosure.
Figure 5:
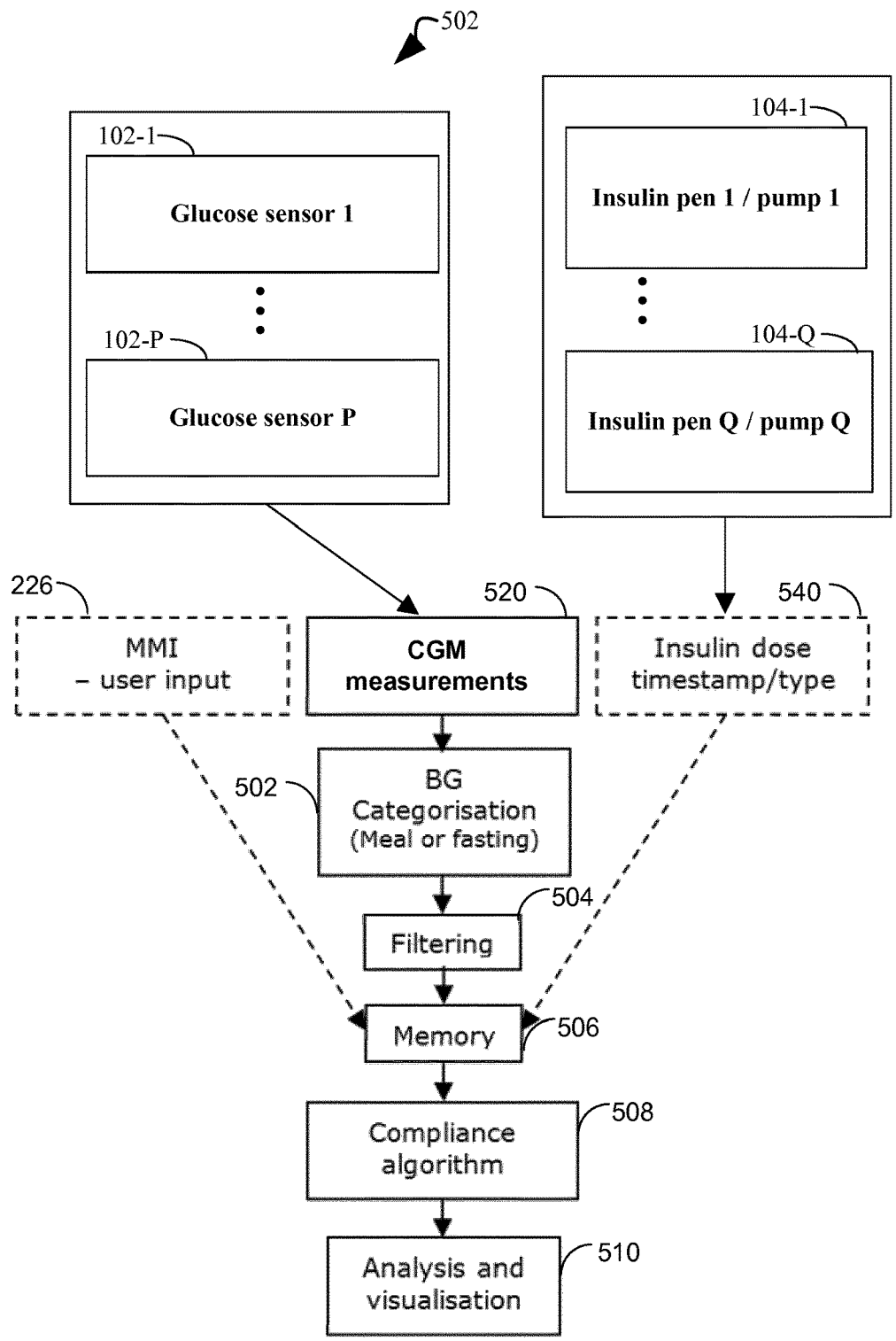
FIG. 5 illustrates an example integrated system of connected insulin pen(s), continuous glucose monitor(s), memory and a processor for performing algorithmic categorization of autonomous glucose data in accordance with an embodiment of the present disclosure.

The present disclosure relies upon the acquisition of data regarding a plurality of metabolic events, such as fasting events or meals, a subject engaged in over a period of time. For each such metabolic event, the data includes a timestamp and a characterization of the metabolic event that is either insulin regimen adherent or insulin regimen nonadherent. FIG. 1 illustrates an example of an integrated system 502 for the acquisition of such data, and FIG. 5 provides more details of such a system 502. The integrated system 502 includes one or more connected insulin pens or pumps 104, one or more continuous glucose monitors 102, memory 506, and a processor (not shown) for performing algorithmic categorization of autonomous glucose data of a subject.

A metabolic event is an event relating to metabolism, which is the sum of the processes in the buildup and destruction of protoplasm, e.g., the chemical changes in living cells by which energy is provided for vital processes and activities and new material is assimilated, i.e., utilized as nourishment.

The metabolism in a living body can be defined in different states: an absorptive state, or fed state, occurs after a meal when the body is digesting food and absorbing nutrients. Digestion begins the moment food enters the mouth, as the food is broken down into its constituent parts to be absorbed through the intestine. The digestion of carbohydrates begins in the mouth, whereas the digestion of proteins and fats begins in the stomach and small intestine. The constituent parts of these carbohydrates, fats, and proteins are transported across the intestinal wall and enter the bloodstream (sugars and amino acids) or the lymphatic system (fats). From the intestines, these systems transport them to the liver, adipose tissue, or muscle cells that will process and use, or store, the energy. In the absorptive state glucose, lipids and amino acids enter the blood stream and insulin may be released (depending on the other conditions like the state and type of diabetes). The postabsorptive state, or the fasting state, occurs when the food has been digested, absorbed, and stored. You commonly fast overnight, but skipping meals during the day puts your body in the postabsorptive state as well. During this state, the body must rely initially on stored glycogen. Glucose levels in the blood begin to drop as it is absorbed and used by the cells. In response to the decrease in glucose, insulin levels also drop. Glycogen and triglyceride storage slows. However, due to the demands of the tissues and organs, blood glucose levels must be maintained in the normal range of 80-120 mg/dL. In response to a drop in blood glucose concentration, the hormone glucagon is released from the alpha cells of the pancreas. Glucagon acts upon the liver cells, where it inhibits the synthesis of glycogen and stimulates the breakdown of stored glycogen back into glucose. This glucose is released from the liver to be used by the peripheral tissues and the brain. As a result, blood glucose levels begin to rise. Gluconeogenesis will also begin in the liver to replace the glucose that has been used by the peripheral tissues. Further information can be found in OpenStax College, Anatomy and Physiology. OpenStax CNX. http://cnx.org/contents/14fb4ad7-39a1-4eee-ab6e-3ef2482e3e22@8.81.

A metabolic event may therefore relate to an event where a certain metabolic state occurs, and the occurrence may be detected by measuring the concentration of an indicator of the event. The metabolic event will be an indicator of the type of state, and the progress of the state, and an indicator of a metabolic event can be the concentration of glucose, glucagon, lipids and amino acids in the blood stream. Other hormones may also be useful for determining events relating to metabolism like cortisol and adrenalin.

Autonomous measurements or autonomous data are measurements or data obtained by a device measuring at a specified or a variable frequency, wherein the measuring is undertaken or carried on without outside control, e.g., when the device is operating in a measurement mode the measuring can be performed without control from the a subject using the device. With the integrated system 502, autonomous timestamped glucose measurements of the subject are obtained 520. Also, data from the one or more insulin pens and/or pumps used to apply a prescribed insulin regimen to the subject is obtained 540 as a plurality of records. Each record comprises a timestamped event specifying an amount of injected (or pumped) insulin medicament that the subject received as part of the prescribed insulin medicament dosage regimen. Fasting events are identified using the autonomous timestamped glucose measurements of the subject. Optionally, meal events are also identified using the autonomous timestamped glucose measurements 502. In this way, the glucose measurements are filtered 504 and stored in nontransitory memory 506.

A metabolic event is characterized as adherent or nonadherent. A metabolic event is adherent when one or more records from the one or more connected insulin pens or pumps 104 temporally and quantitatively establish adherence with the prescribed insulin medicament regimen. Conversely, a metabolic event is characterized as nonadherent when none of the records from the one or more connected insulin pens or pumps 104 temporally and quantitatively establish adherence with the prescribed basal insulin medicament regimen.

Each fasting event is characterized as adherent or nonadherent 508. A fasting event is adherent when one or more records from the one or more connected insulin pens or pumps 104 temporally and quantitatively establish adherence with the prescribed basal insulin medicament regimen during the fasting event. Conversely, a fasting event is characterized as nonadherent when none of the records from the one or more connected insulin pens or pumps 104 temporally and quantitatively establish adherence with the prescribed basal insulin medicament regimen.

A respective meal is deemed bolus regimen adherent when one or more medicament records indicates, on a temporal basis, a quantitative basis and a type of insulin medicament basis, adherence with a prescribed bolus insulin medicament dosage regimen during the respective meal. Conversely, a respective meal is deemed bolus regimen nonadherent when the plurality of medicament records fails to indicate adherence, on a temporal basis, a quantitative basis, and a type of insulin medicament basis, with the prescribed bolus insulin medicament dosage regimen during the respective meal.

This filtered and cataloged glucose data is analyzed and visualized in accordance with the methods of the present disclosure 510. Such visualization enables the subject or health care practitioner to see the effect of insulin regimen adherence on critical subject markers such as blood glucose levels and HbA1c levels.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject" and "user" are used interchangeably herein.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Figure 2:
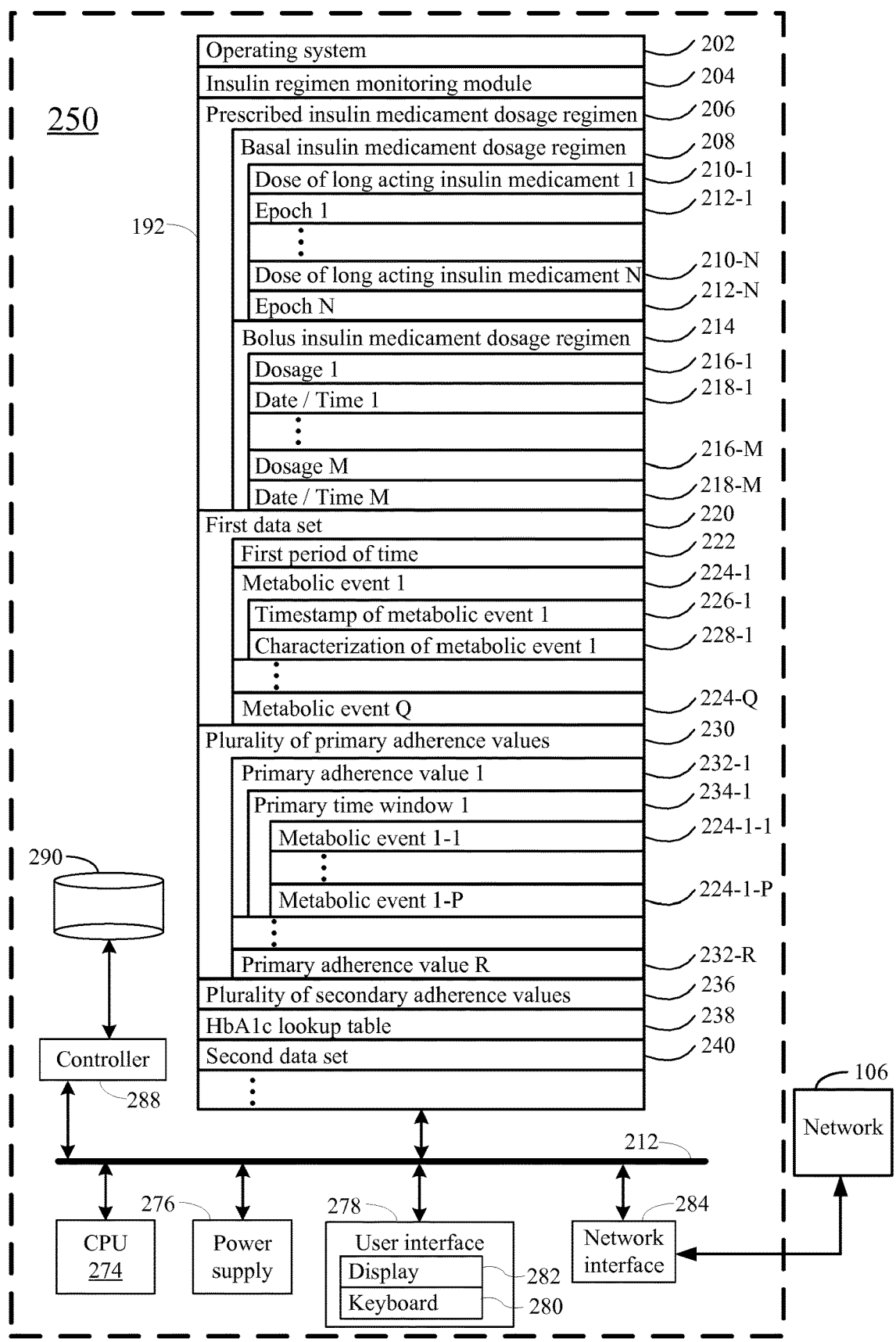
FIG. 2 illustrates a device for monitoring adherence to a prescribed insulin medicament dosage regimen for a subject over time in accordance with an embodiment of the present disclosure.
Figure 3:
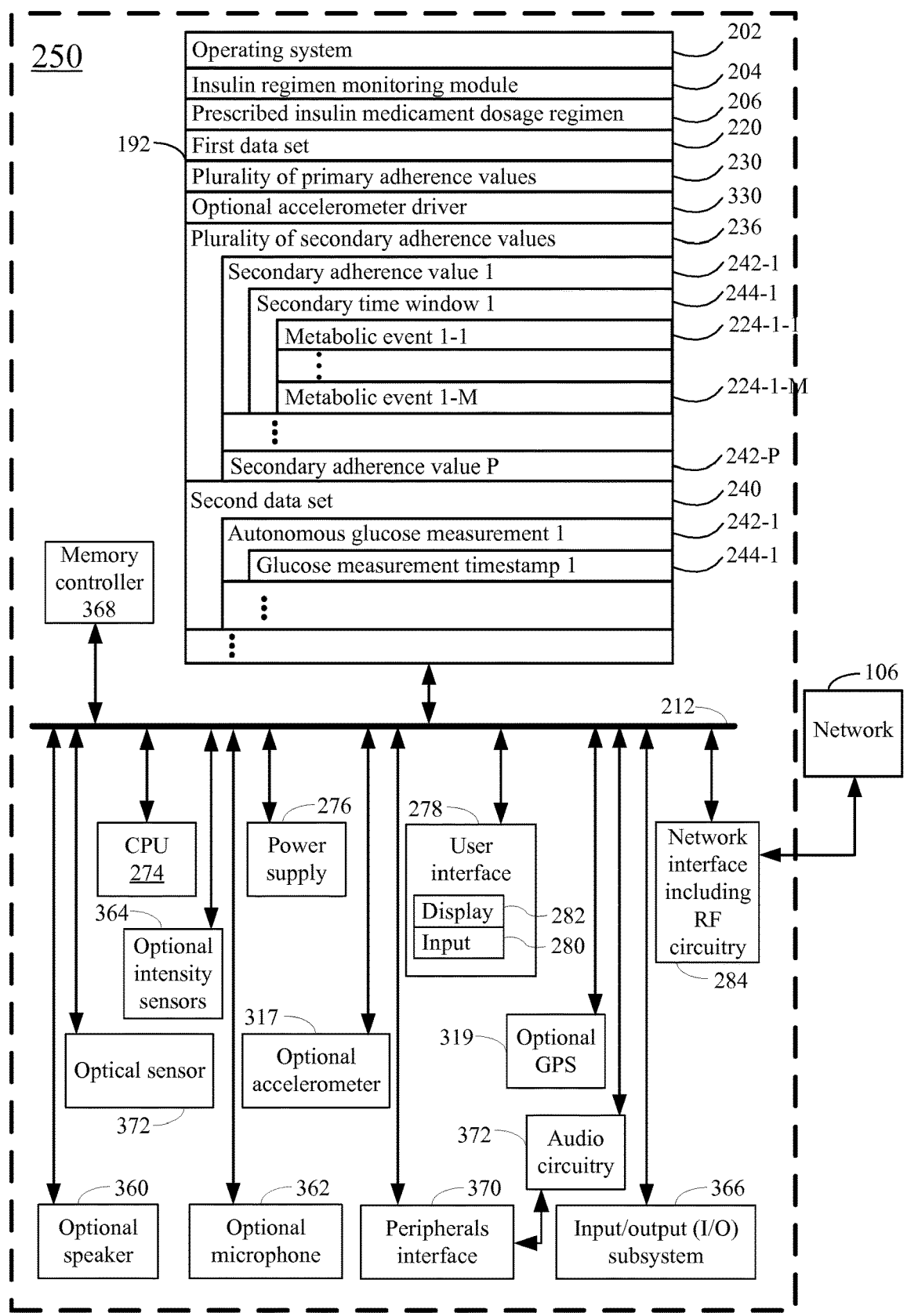
FIG. 3 illustrates a device for monitoring adherence to a prescribed insulin medicament dosage regimen for a subject over time in accordance with another embodiment of the present disclosure.

A detailed description of a system 48 for monitoring adherence to a prescribed insulin medicament dosage regimen 206 for a subject over time in accordance with the present disclosure is described in conjunction with FIGS. 1 through 3. As such, FIGS. 1 through 3 collectively illustrate the topology of the system in accordance with the present disclosure. In the topology, there is a device for monitoring adherence to a prescribed insulin medicament dosage regimen ("monitor device 250") (FIGS. 1, 2, and 3), a device for assessing regimen adherence ("adherence device 200"), one or more glucose sensors 102 associated with the subject (FIG. 1), and one or more insulin pens or pumps 104 for injecting insulin medicaments into the subject (FIG. 1). Throughout the present disclosure, the adherence device 200 and the monitor device 250 will be referenced as separate devices solely for purposes of clarity. That is, the disclosed functionality of the adherence device 200 and the disclosed functionality of the monitor device 250 are contained in separate devices as illustrated in FIG. 1. However, it will be appreciated that, in fact, in some embodiments, the disclosed functionality of the adherence device 200 and the disclosed functionality of the monitor device 250 are contained in a single device.

Referring to FIG. 1, the monitor device 250 monitors adherence to an insulin medicament dosage regimen prescribed to a subject. To do this, the adherence device 200, which is in electrical communication with the monitor device 250, receives autonomous glucose measurements originating from one or more glucose sensors 102 attached to a subject on an ongoing basis. Further, the adherence device 200 receives insulin medicament injection data from one or more insulin pens and/or pumps 104 used by the subject to inject insulin medicaments. In some embodiments, the adherence device 200 receives such data directly from the glucose sensor(s) 102 and insulin pens and/or pumps 104 used by the subject. For instance, in some embodiments the adherence device 200 receives this data wirelessly through radio-frequency signals. In some embodiments such signals are in accordance with an 802.11 (WiFi), Bluetooth, or Zigbee standard. In some embodiments, the adherence device 200 receives such data directly, characterizes metabolic events within the data as regimen adherent or regimen nonadherent, and passes the characterized data to the monitor device 250. In some embodiments the glucose sensor 102 and/or insulin pen/pump includes and RFID tag and communicates to adherence device 200 and/or the monitor device 250 using RFID communication.

In some embodiments, the adherence device 200 and/or the monitor device 250 is not proximate to the subject and/or does not have wireless capabilities or such wireless capabilities are not used for the purpose of acquiring glucose data and insulin medicament injection data. In such embodiments, a communication network 106 may be used to communicate glucose measurements from the glucose sensor 102 to the adherence device 200 and from the one or more insulin pens or pumps 104 to the adherence device 200.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

In some embodiments, there is a single glucose sensor attached to the subject and the adherence device 200 and/or the monitor device 250 is part of the glucose sensor 102. That is, in some embodiments, the adherence device 200 and/or the monitor device 250 and the glucose sensor 102 are a single device.

In some embodiments the adherence device 200 and/or the monitor device 250 is part of an insulin pen or pump 104. That is, in some embodiments, the adherence device 200 and/or the monitor device 250 and an insulin pen or pump 104 are a single device.

Of course, other topologies of system 48 are possible. For instance, rather than relying on a communications network 106, the one or more glucose sensors 102 and the one or more insulin pens and/or pumps 104 may wirelessly transmit information directly to the adherence device 200 and/or monitor device 250. Further, the adherence device 200 and/or the monitor device 250 may constitute a portable electronic device, a server computer, or in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

Referring to FIG. 2, in typical embodiments, the monitor device 250 comprises one or more computers. For purposes of illustration in FIG. 2, the monitor device 250 is represented as a single computer that includes all of the functionality for monitoring adherence to a prescribed insulin medicament dosage regimen. However, the disclosure is not so limited. The functionality for monitoring adherence to a prescribed insulin medicament dosage regimen may be spread across any number of networked computers and/or reside on each of several networked computers and/or by hosted on one or more virtual machines at a remote location accessible across the communications network 106. One of skill in the art will appreciate that a wide array of different computer topologies are possible for the application and all such topologies are within the scope of the present disclosure.

Turning to FIG. 2 with the foregoing in mind, an exemplary monitor device 250 for monitoring adherence to a prescribed insulin medicament dosage regimen comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 212 for interconnecting the aforementioned components, and a power supply 276 for powering the aforementioned components. Data in memory 192 can be seamlessly shared with non-volatile memory 290 using known computing techniques such as caching. Memory 192 and/or memory 290 can include mass storage that is remotely located with respect to the central processing unit(s) 274. In other words, some data stored in memory 192 and/or memory 290 may in fact be hosted on computers that are external to the monitor device 250 but that can be electronically accessed by the monitor device 250 over an Internet, intranet, or other form of network or electronic cable (illustrated as element 106 in FIG. 2) using network interface 284.

The memory 192 of the monitor device 250 for monitoring adherence to a prescribed insulin medicament dosage for a subject stores:
  an operating system 202 that includes procedures for handling various basic system services;
  an insulin regimen monitoring module 204;
  a prescribed insulin medicament dosage regimen 206 for a subject, the prescribed insulin medicament dosage regimen comprising a basal insulin medicament dosage regimen 208 and, optionally in some embodiments, a bolus insulin medicament dosage regimen 214;
  a first data set 220, the first data set representing a first period of time 222 and comprising a plurality of metabolic events the subject engaged in during this first period of time and, for each respective metabolic event 224 in the plurality of metabolic events, a timestamp 226 representing when the respective metabolic event occurred as well as a characterization 228 of the respective metabolic event;
  a plurality of primary adherence values 230 for the subject, each respective primary adherence value 232 in the plurality of primary adherence values representing a corresponding primary time window 234 in a plurality of primary time windows within the first period of time;
  an optional plurality of secondary adherence values 236 for the subject;
  an optional HbA1c lookup table; and
  an optional second data set for the subject.
  In some embodiments, the insulin regimen monitoring module 204 is accessible within any browser (phone, tablet, laptop/desktop). In some embodiments the insulin regimen monitoring module 204 runs on native device frameworks, and is available for download onto the monitor device 250 running an operating system 202 such as Android or iOS.

In some implementations, one or more of the above identified data elements or modules of the monitor device 250 for monitoring adherence to a prescribed insulin medicament dosage regimen for a subject over time are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above.

In some embodiments, a monitor device 250 for monitoring adherence to a prescribed insulin medicament dosage regimen 206 for a subject over time is a smart phone (e.g., an iPHONE), laptop, tablet computer, desktop computer, or other form of electronic device (e.g., a gaming console). In some embodiments, the monitor device 250 is not mobile. In some embodiments, the monitor device 250 is mobile.

FIG. 3 provides a further description of a specific embodiment of a monitor device 250 that can be used with the instant disclosure. The monitor device 250 illustrated in FIG. 3 has one or more processing units (CPU's) 274, peripherals interface 370, memory controller 368, a network or other communications interface 284, a memory 192 (e.g., random access memory), a user interface 278, the user interface 278 including a display 282 and input 280 (e.g., keyboard, keypad, touch screen), an optional accelerometer 317, an optional GPS 319, optional audio circuitry 372, an optional speaker 360, an optional microphone 362, one or more optional intensity sensors 364 for detecting intensity of contacts on the monitor device 250 (e.g., a touch-sensitive surface such as a touch-sensitive display system 282 of the monitor device 250), an optional input/output (I/O) subsystem 366, one or more optional optical sensors 372, one or more communication busses 212 for interconnecting the aforementioned components, and a power system 276 for powering the aforementioned components.

In some embodiments, the input 280 is a touch-sensitive display, such as a touch-sensitive surface. In some embodiments, the user interface 278 includes one or more soft keyboard embodiments. The soft keyboard embodiments may include standard (QWERTY) and/or non-standard configurations of symbols on the displayed icons.

The monitor device 250 illustrated in FIG. 3 optionally includes, in addition to accelerometer(s) 317, a magnetometer (not shown) and a GPS 319 (or GLONASS or other global navigation system) receiver for obtaining information concerning the location and orientation (e.g., portrait or landscape) of the monitor device 250 and/or for determining an amount of physical exertion by the subject.

It should be appreciated that the monitor device 250 illustrated in FIG. 3 is only one example of a multifunction device that may be used for monitoring adherence to a prescribed insulin medicament dosage regimen 206 for a subject over time, and that the monitor device 250 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 192 of the monitor device 250 illustrated in FIG. 3 optionally includes high-speed random access memory and optionally also includes non-volatile memory, such as one or more magnetic disk storage devices, flash memory devices, or other non-volatile solid-state memory devices.

Access to memory 192 by other components of the monitor device 250, such as CPU(s) 274 is, optionally, controlled by the memory controller 368.

The peripherals interface 370 can be used to couple input and output peripherals of the device to CPU(s) 274 and memory 192. The one or more processors 274 run or execute various software programs and/or sets of instructions stored in memory 192, such as the insulin regimen monitoring module 204, to perform various functions for the monitoring device 250 and to process data.

In some embodiments, the peripherals interface 370, CPU(s) 274, and memory controller 368 are, optionally, implemented on a single chip. In some other embodiments, they are, optionally, implemented on separate chips.

RF (radio frequency) circuitry of network interface 284 receives and sends RF signals, also called electromagnetic signals. In some embodiments, prescribed insulin medicament dosage regimen, first data set 220, HbA1c lookup table 238, and/or second data set 240 is received using this RF circuitry from one or more devices such as a glucose sensor 102 associated with a subject an insulin pen or pump 104 associated with the subject and/or the adherence device 200. In some embodiments, the RF circuitry 108 converts electrical signals to/from electromagnetic signals and communicates with communications networks and other communications devices, glucose sensors 102, and insulin pens or pumps 104 and/or the adherence device 200 via the electromagnetic signals. RF circuitry 284 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 284 optionally communicates with the communication network 106. In some embodiments, the circuitry 284 does not include RF circuitry and, in fact, is connected to the network 106 through one or more hard wires (e.g., an optical cable, a coaxial cable, or the like).

In some embodiments, audio circuitry 372, optional speaker 360, and optional microphone 362 provide an audio interface between the subject and the monitor device 250. The audio circuitry 372 receives audio data from peripherals interface 370, converts the audio data to electrical signals, and transmits the electrical signals to speaker 360. Speaker 360 converts the electrical signals to human-audible sound waves. Audio circuitry 372 also receives electrical signals converted by the microphone 362 from sound waves. Audio circuitry 372 converts the electrical signal to audio data and transmits the audio data to peripherals interface 370 for processing. Audio data is, optionally, retrieved from and/or transmitted to memory 192 and/or RF circuitry 284 by peripherals interface 370.

In some embodiments, the power supply 276 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the monitor device 250 optionally also includes one or more optical sensors 372. The optical sensor(s) 372 optionally include charge-coupled device (CCD) or complementary metal-oxide semiconductor (CMOS) phototransistors. The optical sensor(s) 372 receive light from the environment, projected through one or more lens, and converts the light to data representing an image. The optical sensor(s) 372 optionally capture still images and/or video. In some embodiments, an optical sensor is located on the back of the monitor device 250, opposite the display 282 on the front of the device 250, so that the input 280 is enabled for use as a viewfinder for still and/or video image acquisition. In some embodiments, another optical sensor 372 is located on the front of the monitor device 250 so that the subject's image is obtained (e.g., to verify the health or condition of the subject, to determine the physical activity level of the subject, or to help diagnose a subject's condition remotely, etc.).

As illustrated in FIG. 3, a monitor device 250 preferably comprises an operating system 202 that includes procedures for handling various basic system services. The operating system 202 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments the monitor device 250 is a smart phone. In other embodiments, the monitor device 250 is not a smart phone but rather is a tablet computer, desktop computer, emergency vehicle computer, or other form or wired or wireless networked device. In some embodiments, the monitor device 250 has any or all of the circuitry, hardware components, and software components found in the monitor device 250 depicted in FIG. 2 or 3. In the interest of brevity and clarity, only a few of the possible components of the monitor device 250 are shown in order to better emphasize the additional software modules that are installed on the monitor device 250.

While the system 48 disclosed in FIG. 1 can work standalone, in some embodiments it can also be linked with electronic medical records to exchange information in any way.

Figure 4B:
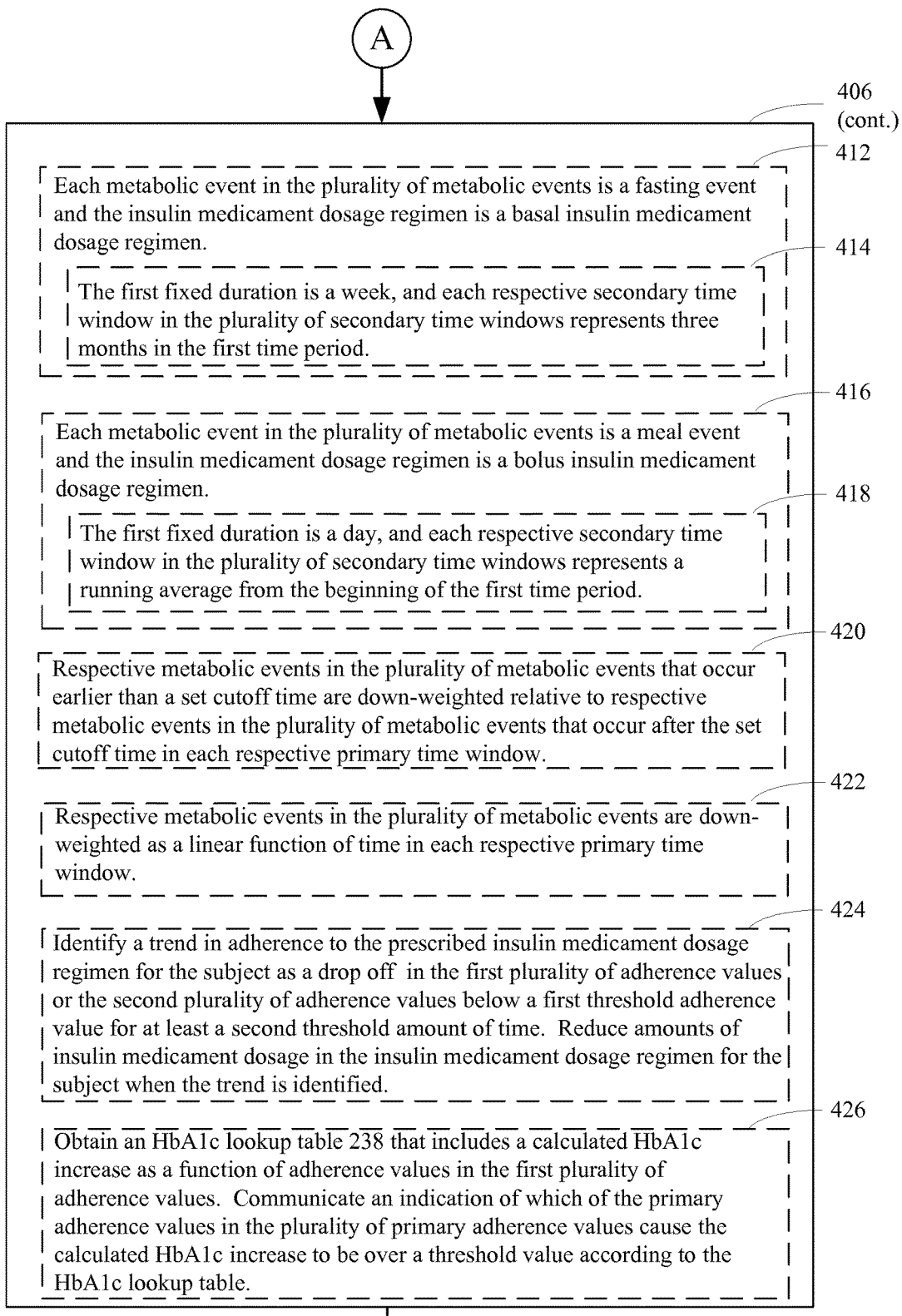
Figure 4C:
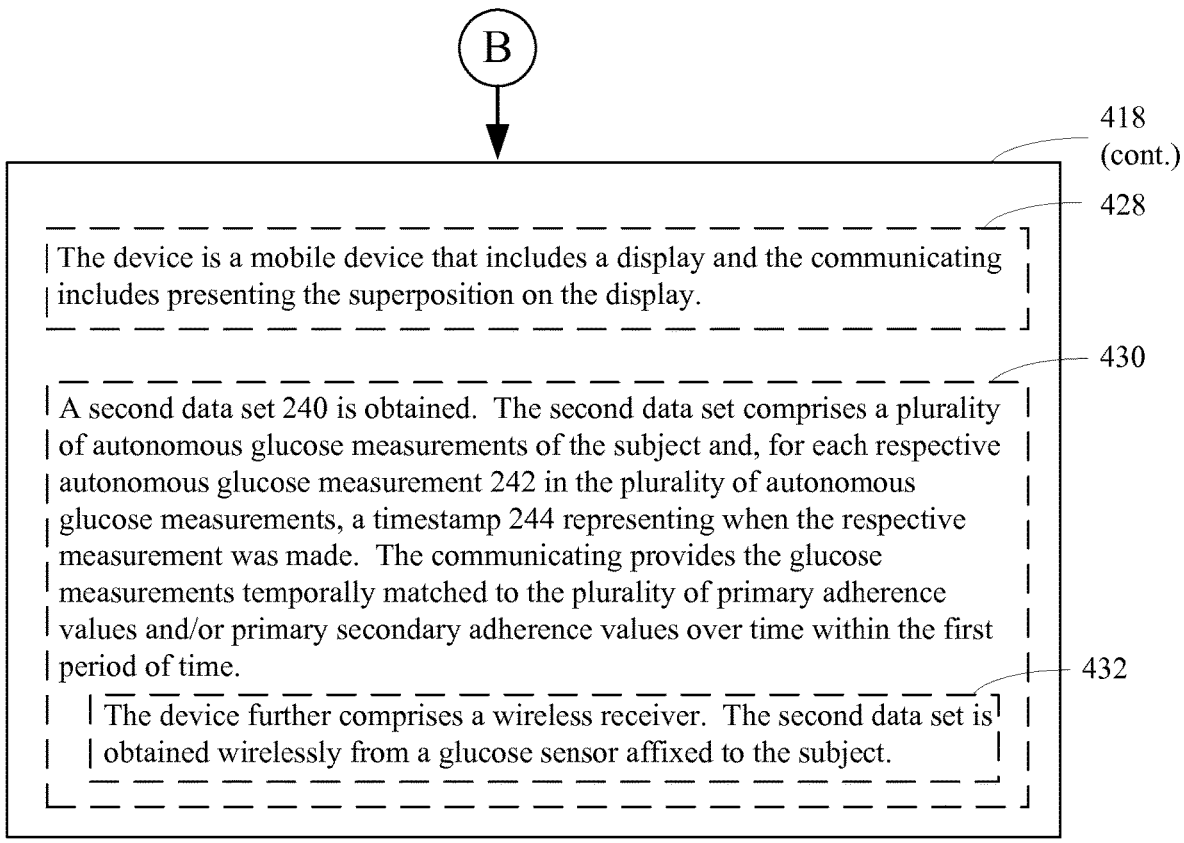

Now that details of a system 48 for monitoring adherence to a prescribed insulin medicament dosage regimen 206 for a subject over time been disclosed, details regarding a flow chart of processes and features of the system, in accordance with an embodiment of the present disclosure, are disclosed with reference to FIGS. 4A through 4C. In some embodiments, such processes and features of the system are carried out by the insulin regimen monitoring module 204 illustrated in FIGS. 2 and 3.

Block 402. With reference to block 402 of FIG. 4A, the goal of insulin therapy in subjects with either type 1 diabetes mellitus or type 2 diabetes mellitus is to match as closely as possible normal physiologic insulin secretion to control fasting and postprandial plasma glucose. This is done with a prescribed insulin medicament dosage regimen 206 for the subject. One aspect of the present disclosure provides a monitoring device 250 for monitoring adherence to a prescribed insulin medicament dosage regimen 206 for a subject over time. In the present disclosure, the prescribed insulin medicament dosage regimen comprises a basal insulin medicament dosage regimen 208. The monitoring device comprises one or more processors 274 and a memory 192/290. The memory stores instructions that, when executed by the one or more processors, perform a method. In the method, a first data set 220 is obtained.

The first data set comprises a plurality of metabolic events in which the subject engaged. The plurality of metabolic events is within a first period of time 222. In varying embodiments, the first period of time is one day or more, three days or more, five days or more, ten days or more, one month or more, two months or more, three months or more or five months or more. Each respective metabolic event 224 in the plurality of metabolic events comprises (i) a timestamp 226 of the respective metabolic event and (ii) a first characterization 228 that is one of insulin regimen adherent and insulin regimen nonadherent.

In some embodiments each metabolic event 224 in the first data set 220 has one or more characterizations 228 set forth in Table 1.

TABLE 1

Exemplary characterizations 228 of metabolic events 224.

| | Category A |
|---|---|
| A1 | In Bolus Adherence |
| A2 | Out of Bolus Adherence |
| | Category B |
| B1 | In Basal Adherence |
| B2 | Out of Basal Adherence |
| | Category C |
| C1 | In timing adherence |
| C2 | Out of timing adherence |
| | Category D |
| D1 | In dose size adherence |
| D2 | Out of dose size adherence |

Using the characterizations set forth in Table 1, the same period of time can contain metabolic events with different labels. For instance, a whole day can contain a metabolic event (fasting event) marked as out of basal adherence, B2, but three metabolic events (meal events) within that day can be labelled in bolus adherence, A1. FIG. 15 illustrates an algorithm for characterizing a metabolic event, wherein the example is a fasting event, and wherein the relevant period of time defined by the regimen is one day. The characterization is provided in accordance with the categories of Table 1. In such embodiments, continuously marked periods, e.g. primary period being a day, contains a fasting event marked with B2 or a meal events marked with A1, are referred to as characterized metabolic events. As another example, consider the case where three fasting events within each of the first three days of a period of one week are marked as in 100% basal adherence (e.g. in basal and timing adherence B1, C1), two fasting events within each of the two following days are marked as in 50% basal adherence (e.g. in basal adherence but out of timing adherence), and two fasting events within the last two days are marked as in 0% basal adherence (e.g. out of basal adherence and out of timing adherence B2, C2). In the case where a fasting event is characterized and marked as in basal and timing adherence the event can as an example be defined as 100% insulin regimen adherent, in the case where the metabolic event is marked in basal adherence, but out of timing adherence the event can as an example be defined as 50% insulin regimen adherent, this could be a different percentage, based on estimated effect of taking a dose later than recommended. In the case where the fasting event is out of basal adherence the event is 0% insulin regimen adherent corresponding to insulin regimen nonadherent. The number of insulin regimen adherent metabolic events in the example is thus 3+2*50%+2*0%. In this example the past week's adherence (primary adherence value 232 for the primary time window 234 of the past week) is thus:

$$\text{Past 7 days' adherence} = \frac{3 + 0.5 * 2}{7} = \frac{4}{7} = 57\%$$

In other embodiments, such characterizations are imposed by considering metabolic events to be fasting events or meal events and characterizing each fasting event or meal event for insulin medicament regimen adherence.

In some embodiments, metabolic events can be a metabolic events defined in the medicament regimen, which can be automatically identified from a device continuously measuring an indicator of an event relating, wherein the event is relating to a metabolic state of the subject, whereby the device allows the metabolic event to be timestamped and to be characterized with respect to the medicament regimen as regimen adherent or regimen nonadherent. For example, a metabolic event defined according to the medicament regimen could be a meal event, wherein the medicament regimen determines that bolus insulin should be administered based on glucose measurements relating to this event, or it could be a fasting event, wherein the medicament regimen determines that basal insulin should be administered based on glucose measurements relating to this event.

In some embodiments, metabolic events (e.g., meal events, fasting events, etc.) incurred by the subject are identified without reliance on records kept by the subject. For instance, in some embodiments a second data set 240 comprising autonomous glucose measurements 242 of the subject from one or more glucose sensors 102 is obtained. Each such autonomous glucose measurement 242 is timestamped with a glucose measurement timestamp 244 to represent when the respective measurement was made.

The FREESTYLE LIBRE CGM by ABBOTT ("LIBRE") is an example of a glucose sensor that may be used as a glucose sensor 102. The LIBRE allows calibration-free glucose measurements with an on-skin coin-sized sensor, which can send up to eight hours of data to a reader device (e.g., the adherence device 200 and/or the monitor device 250) via near field communications, when brought close together. The LIBRE can be worn for fourteen days in all daily life activities. In some embodiments, autonomous glucose measurements are taken from the subject at an interval rate of 5 minutes or less, 3 minutes or less, or 1 minute or less. In some cases the sampling rate may vary during sampling. Example 1 below illustrates how such autonomous glucose measurements are used to both identify metabolic events and to characterize each of them as insulin regimen adherent or insulin regimen nonadherent.

Figure 6:
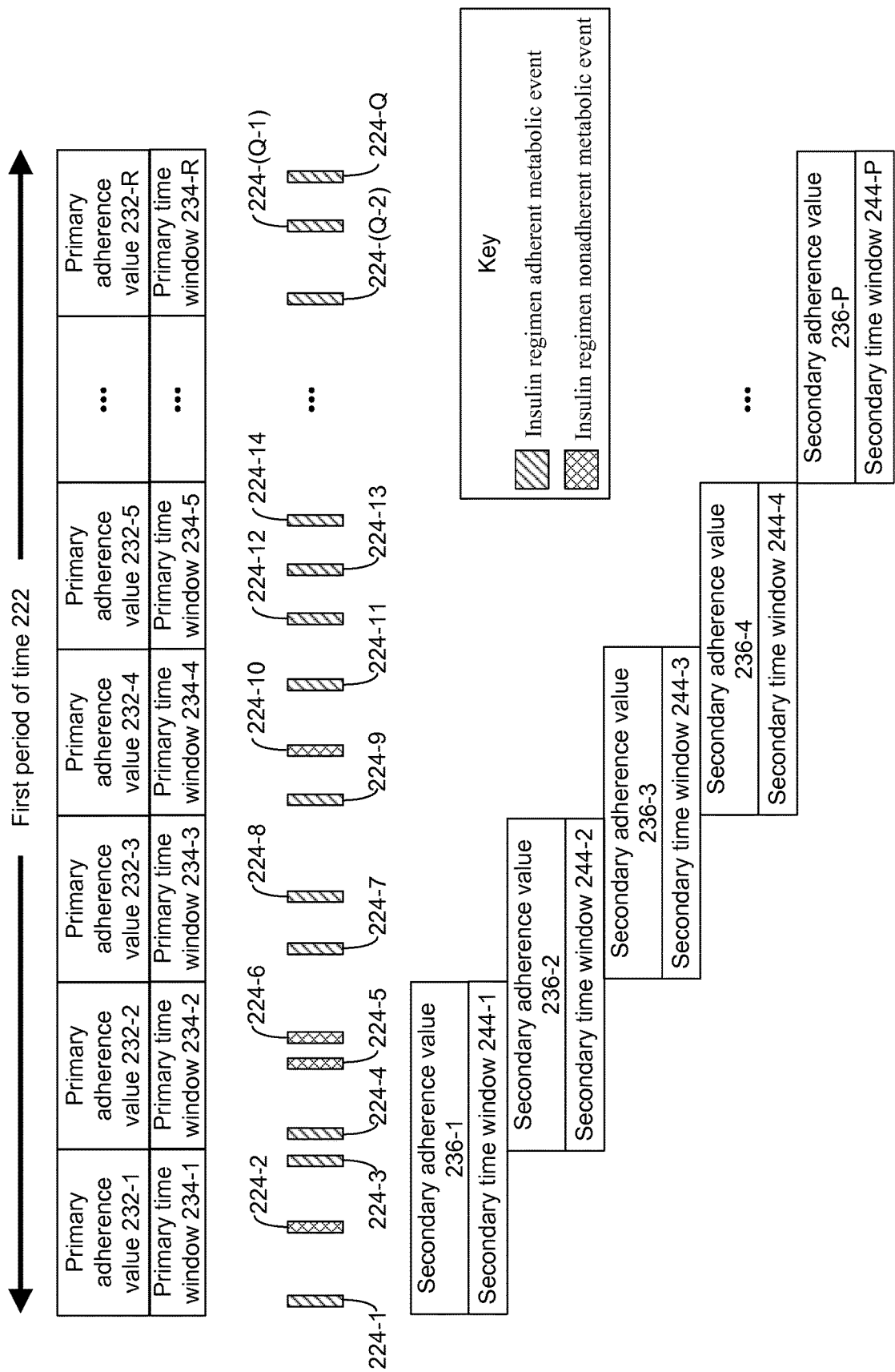
FIG. 6 illustrates the temporal relationship between primary adherence values, primary time windows, metabolic events, secondary adherence values and secondary time windows in accordance with an embodiment of the present disclosure.

Block 404. Referring to block 404 of FIG. 4A, the process continues with the computation of a plurality of primary adherence values 230. Each respective primary adherence value 232 in the plurality of primary adherence values represents a corresponding primary time window 232 in a plurality of primary time windows within the first period of time. Each primary time window is of a same first fixed duration. FIG. 6 illustrates. In FIG. 6, the first period of time 222 is illustrated as a timeline. Each primary time window 234, and its corresponding primary adherence value 232, is allocated an equal portion of this timeline.

Each respective primary adherence value 232 in the plurality of primary adherence values is computed by dividing a number of insulin regimen adherent metabolic events by a total number of metabolic events in the plurality of metabolic events that have timestamps in the primary time window 234 corresponding to the respective primary adherence value 232. For example, consider the primary time window 234-1 of FIG. 6 in which there are two insulin regimen adherent metabolic events (224-1 and 224-3) and one insulin regimen nonadherent metabolic event for a total of three metabolic events 224 in the primary time window 234-1. In this example, the primary adherence value 232-1 is computed by dividing the number of insulin regimen adherent metabolic events in the corresponding primary time window 234-1 (two, 224-1 and 224-3) by the total number of metabolic events that have timestamps in the corresponding primary time window (three, 224-1, 224-2, and 224-3), that is dividing "2" by "3." It will be appreciated that the process of dividing a number of insulin regimen adherent metabolic events by a total number of metabolic events in the plurality of metabolic events can be done any number of ways and all such ways are encompassed by the phrase "dividing a number of insulin regimen adherent metabolic events by a total number of metabolic events in the plurality of metabolic events." For instance, the division can be effectuated by, in fact, multiplying a number of insulin regimen adherent metabolic events by the inverse of the total number of metabolic events in the plurality of metabolic events (e.g., in the example above, by computing (2*(1/3)).

Figure 7:
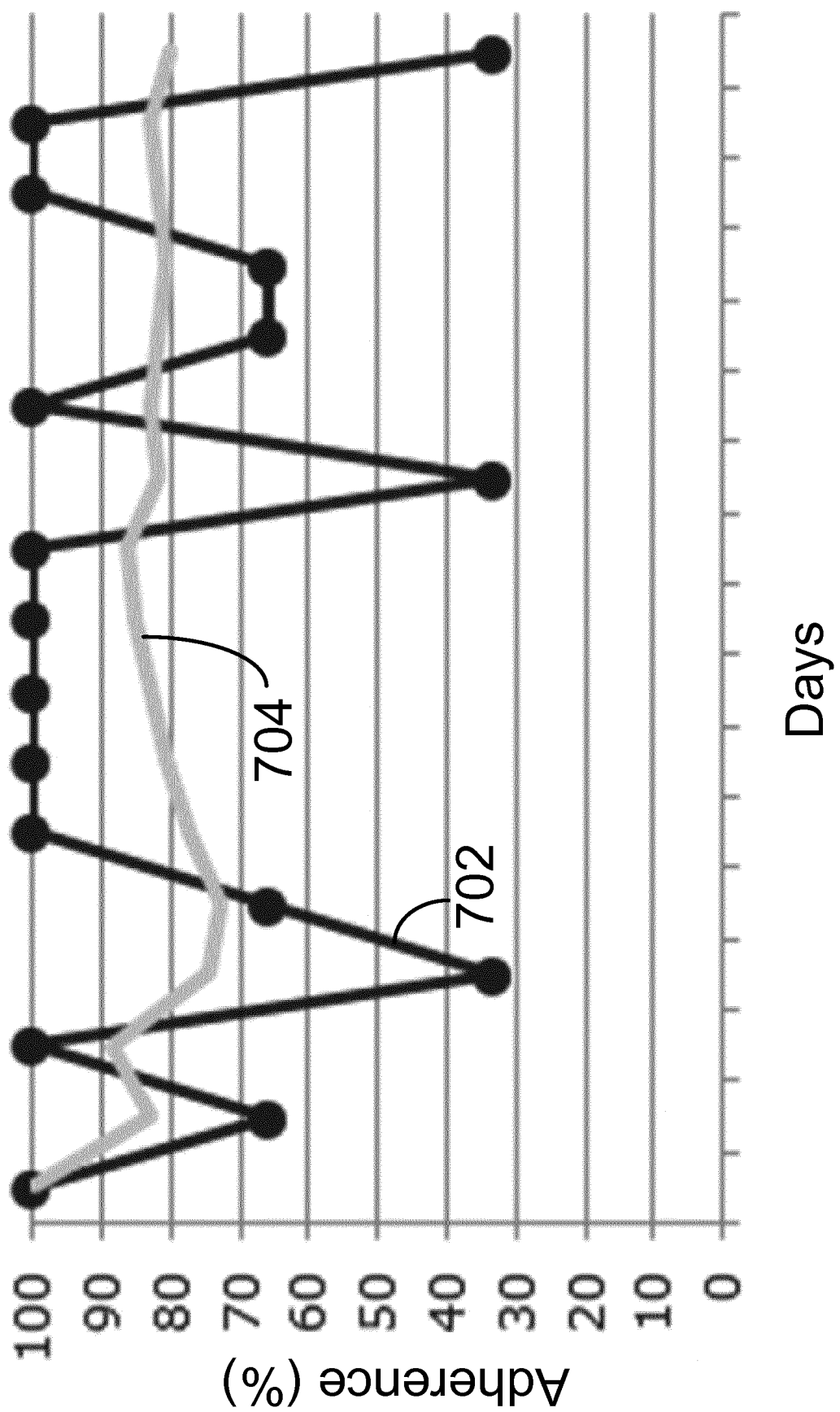
FIG. 7 illustrates the communication of a superposition of primary adherence values and secondary adherence values across a first period of time in accordance with an embodiment of the present disclosure.

Block 406. Referring to block 404 of FIG. 4A, the plurality of primary adherence values 230 is communicated across the first period of time 222 thereby monitoring adherence to the prescribed insulin medicament dosage regimen for the subject over time. FIG. 7 illustrates. In FIG. 7, each adherence values 230 in the plurality of primary adherence values is communicated as a data point on the line 702.

In one such embodiment, the metabolic events 224 are meal events, each primary time window 234 is one day, and the plurality of primary adherence values 232 of line 702 represent daily bolus adherence.

In other embodiment, the metabolic events 224 are meal events, each primary time window 234 is 4 hours, 8 hours, 12 hours, 24 hours, 48 hours, 72 hours or four days, and the plurality of primary adherence values 232 of line 702 represent bolus adherence.

As FIG. 7 further illustrates, in some embodiments, secondary adherence values 236 are plotted along a line 704 along with the primary adherence values on the line 702. For instance, as illustrated in block 408 of FIG. 4A, in some embodiments, a plurality of secondary adherence values 236 is computed. Each respective secondary adherence value in the plurality of secondary adherence values represents a corresponding secondary time window 244 in a plurality of contemporaneously overlapping secondary time windows within the first period of time. FIG. 6 illustrates.

In FIG. 6, each secondary time window 244, and its corresponding secondary adherence value 244, is allocated a portion of the first period of time. However, each respective secondary time window 244 in the plurality of secondary time windows 244 is contemporaneously overlapping at least one other secondary time window 244 in the plurality of secondary time windows 244 along this the time line. Each respective secondary adherence value 236 in the plurality of secondary adherence values is computed by dividing a number of metabolic events 224 that are insulin regimen adherent by a total number of metabolic events in the plurality of metabolic events that have timestamps in the secondary time window corresponding to the respective secondary adherence value. For example, consider the secondary time window 244-1 of FIG. 6 in which there are three insulin regimen adherent metabolic events (224-1, 224-3, and 224-4) and three insulin regimen nonadherent metabolic events (224-2, 224-5 and 224-6) for a total of six metabolic events 224 in the secondary time window 244-1. In this example, the secondary adherence value 236-1 is computed by dividing the number of insulin regimen adherent metabolic events in the corresponding secondary time window 236-1 (three, 224-1, 224-3, and 224-3) by the total number of metabolic events that have timestamps in the corresponding secondary time window (six, 224-1 through -6), that is dividing "3" by "6." It will be appreciated that the process of dividing a number of insulin regimen adherent metabolic events by a total number of metabolic events in the plurality of metabolic events can be done any number of ways and all such ways are encompassed by the phrase "dividing a number of insulin regimen adherent metabolic events by a total number of metabolic events in the plurality of metabolic events." For instance, the division can be effectuated by, in fact, multiplying a number of insulin regimen adherent metabolic events by the inverse of the total number of metabolic events in the plurality of metabolic events (e.g., in the example above, by computing (3*(1/6)).

As illustrated in FIG. 6, each secondary time window 244 in at least a subset of the secondary time windows in the plurality of secondary time windows is of longer duration than the first fixed duration that sets the duration of the primary time window. In FIG. 6, the secondary time windows are each the same length and are exactly twice as long as the primary time windows 234. In various other embodiments, the secondary time windows are each the same length and are exactly three times as long as, exactly four times as long as, exactly five times as long as, exactly six times as long as, exactly seven times as long as, exactly eight times as long as, exactly nine times as long as, or exactly ten times as long as the primary time windows 234.

In some embodiments each secondary time window 244 is one week long and each respective secondary time window 244 overlaps another respective secondary time window 244 by six days. In some embodiments each secondary time window 244 is one week long and each respective secondary time window 244 overlaps another respective secondary time window 244 by one day, two days, three days, four days, five days, or six days. In some embodiments each secondary time window 244 is one week long or longer and each respective secondary time window 244 does not overlap any other secondary time window 244.

In some embodiments, each respective secondary time window 244 exhibits fifty percent temporal overlap with another secondary time window in the plurality of time windows, with respect to the length of time of the respective secondary time window 244, as illustrated in FIG. 6. In some embodiments, each respective secondary time window 244 exhibits less than ten percent temporal overlap with another secondary time window in the plurality of time windows, with respect to the length of time of the respective secondary time window 244. In some embodiments, each respective secondary time window 244 exhibits between ten percent and thirty percent temporal overlap with another secondary time window in the plurality of time windows with respect to the length of time of the respective secondary time window 244. In some embodiments, each respective secondary time window 244 exhibits between thirty percent and sixty percent temporal overlap with another secondary time window in the plurality of time windows with respect to the length of time of the respective secondary time window 244. In some embodiments, each respective secondary time window 244 exhibits between sixty percent and ninety percent temporal overlap with another secondary time window in the plurality of time windows with respect to the length of time of the respective secondary time window 244.

As illustrated in FIG. 7, in embodiments where both primary and secondary adherence values are computed, the communicating step comprises communicating a superposition of the plurality of primary adherence values and the plurality of secondary adherence values across the first period of time. In FIG. 7, the plurality of primary adherence values is communicated as line 602 whereas the plurality of secondary adherence values is communicated as line 704. In some embodiments, calculated primary adherence values 232 and/or secondary adherence values 244 are scaled so that they fall into a range other than their native range. Thus, in some embodiments, the native range of the calculated primary adherence values 232 and/or secondary adherence values 244 is zero to 1, but they are then uniformly scaled to zero to 100, zero to 1000, or any other suitable scale. Such scaling acts independently of any downweighting of metabolic events 224.

In some embodiments, the adherence device 250 allows a subject to add and mark events manually. In some such embodiments, the adherence device 250 suggests categories for the subject to choose from, e.g. events such as meals, insulin and glucose measurements, sleeping periods, periods of physical activity, sick days. In some embodiments, these events are marked with a specific category name, which is then used to identify causes of poor glycaemic control and provide improved treatment transparency. For instance, in some embodiments this is accomplished by temporally superimposing these additional events onto the primary adherence values and/or secondary adherence values and displaying the superposition on the display of the monitor device 250. In some embodiments, these additional events are detected by a wearable device.

Figure 11:
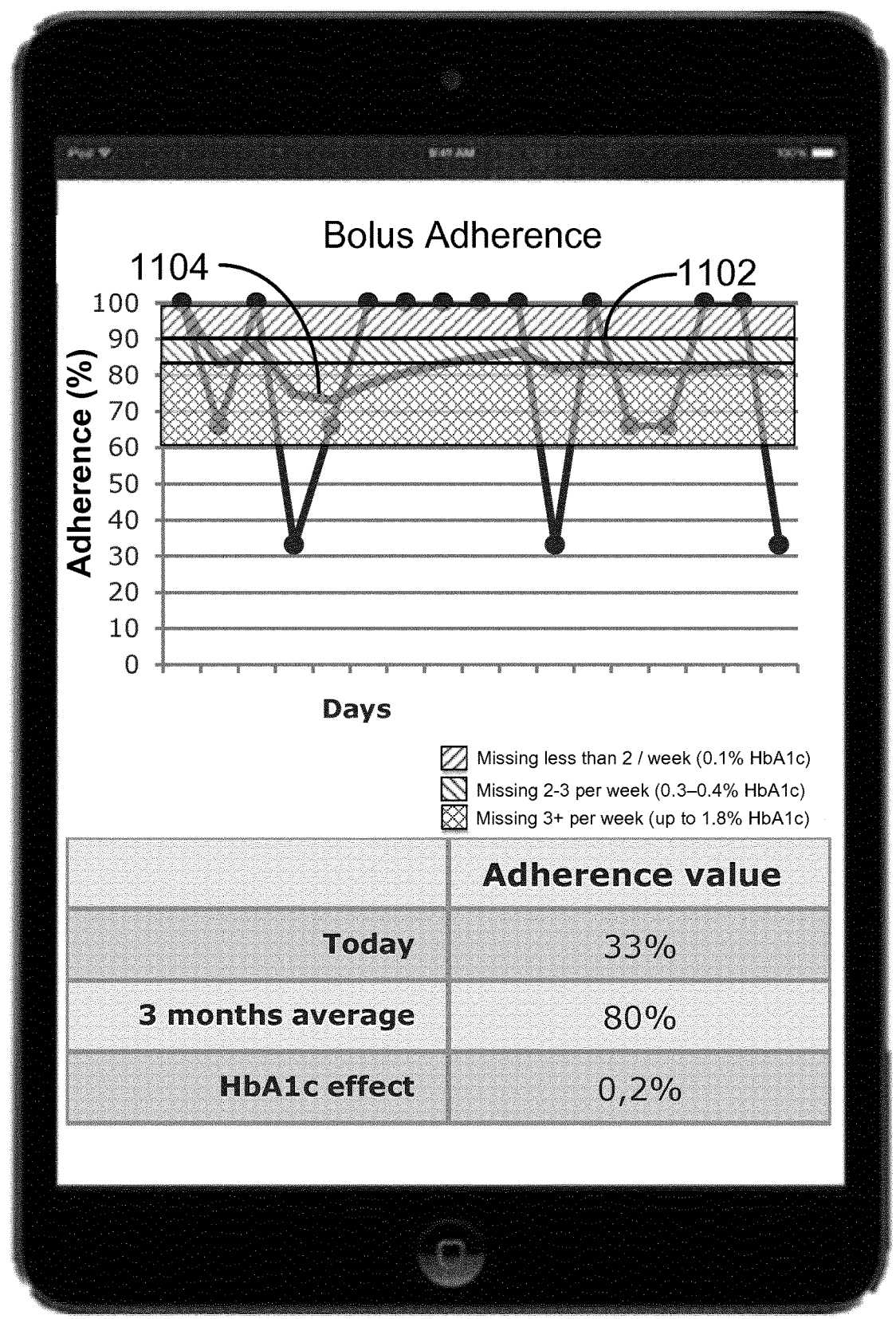
FIG. 11 illustrates an example of how bolus adherence is communicated in accordance with another embodiment of the present disclosure.
Figure 12:
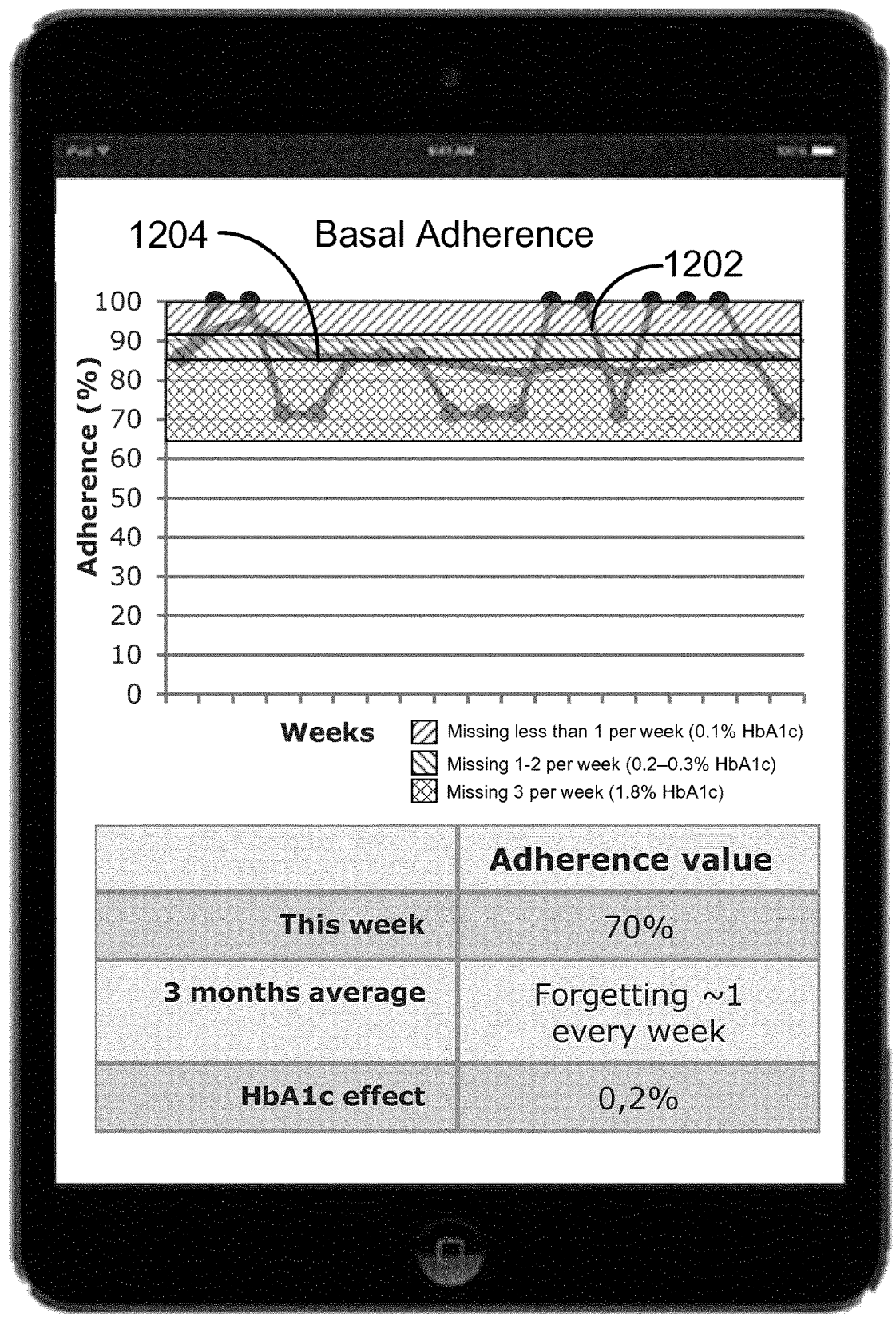
FIG. 12 illustrates an example of how basal adherence is communicated in accordance with another embodiment of the present disclosure.

Referring to block 410 of FIG. 4A, in some embodiments, each secondary time window 244 is of a same second fixed duration that is greater than the first fixed duration of the primary time windows. This is illustrated in FIG. 6 where it can be seen that the secondary time window 244 are a longer fixed duration than the primary time windows 234. FIG. 11 illustrates an example of how bolus adherence is communicated in accordance with an embodiment of the present disclosure, in which line 1102 is the primary adherence values and line 1104 is the secondary adherence values. FIG. 12 illustrates an example of how basal adherence is communicated in accordance with an embodiment of the present disclosure, in which line 1202 is the primary adherence values and line 1204 is the secondary adherence values.

Figure 8:
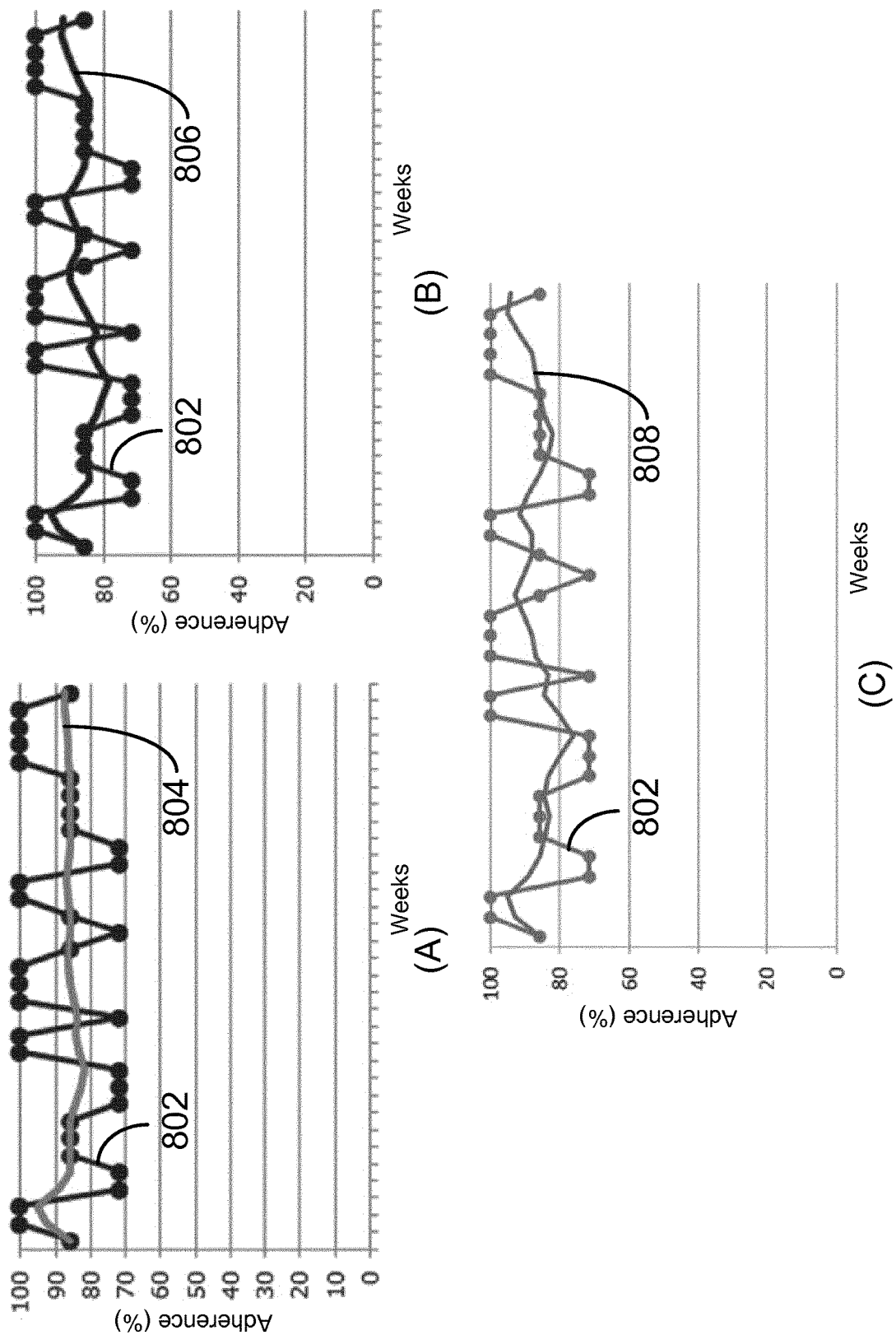
FIG. 8A illustrates the communication of a superposition of primary adherence values and secondary adherence values across a first period of time, where each of the primary adherence values represents weekly basal adherence, and each of the secondary adherence values is a running unweighted average adherence over a number of weeks, in accordance with an embodiment of the present disclosure.
FIG. 8B illustrates the communication of a superposition of primary adherence values and secondary adherence values across a first period of time, where each of the primary adherence values represents weekly basal adherence, and each of the secondary adherence values is a running average adherence, weighted linearly with time over a number of weeks, in accordance with an embodiment of the present disclosure.
FIG. 8C illustrates the communication of a superposition of primary adherence values and secondary adherence values across a first period of time, where each of the primary adherence values represents weekly basal adherence, and each of the secondary adherence values is a running average adherence, weighted such that the past four weeks are weighted 100% and weeks prior to the past four weeks are weighted fifty percent, in accordance with an embodiment of the present disclosure.

Referring to block 412 of FIG. 4B, in some embodiments, each metabolic event 224 in the plurality of metabolic events is a fasting event and the prescribed insulin medicament dosage regimen 206 is a basal insulin medicament dosage regimen 208. In some such embodiments, the first fixed duration of each primary time window 234 is a week, and each respective secondary time window in the plurality of secondary time windows represents three months in the first time period. Communication of primary adherence values 232 and secondary adherence values 242 in accordance with such embodiments is illustrated in FIG. 8A, where the primary adherence values 232 are reported as line 802 and the secondary adherence values 242 are reported as line 804. The communication of regimen adherence data in this way is highly advantageous, because the user can ascertain not only the weekly basal adherence from line 802, but also get a more time averaged perspective of regimen adherence from line 804.

Figure 13:
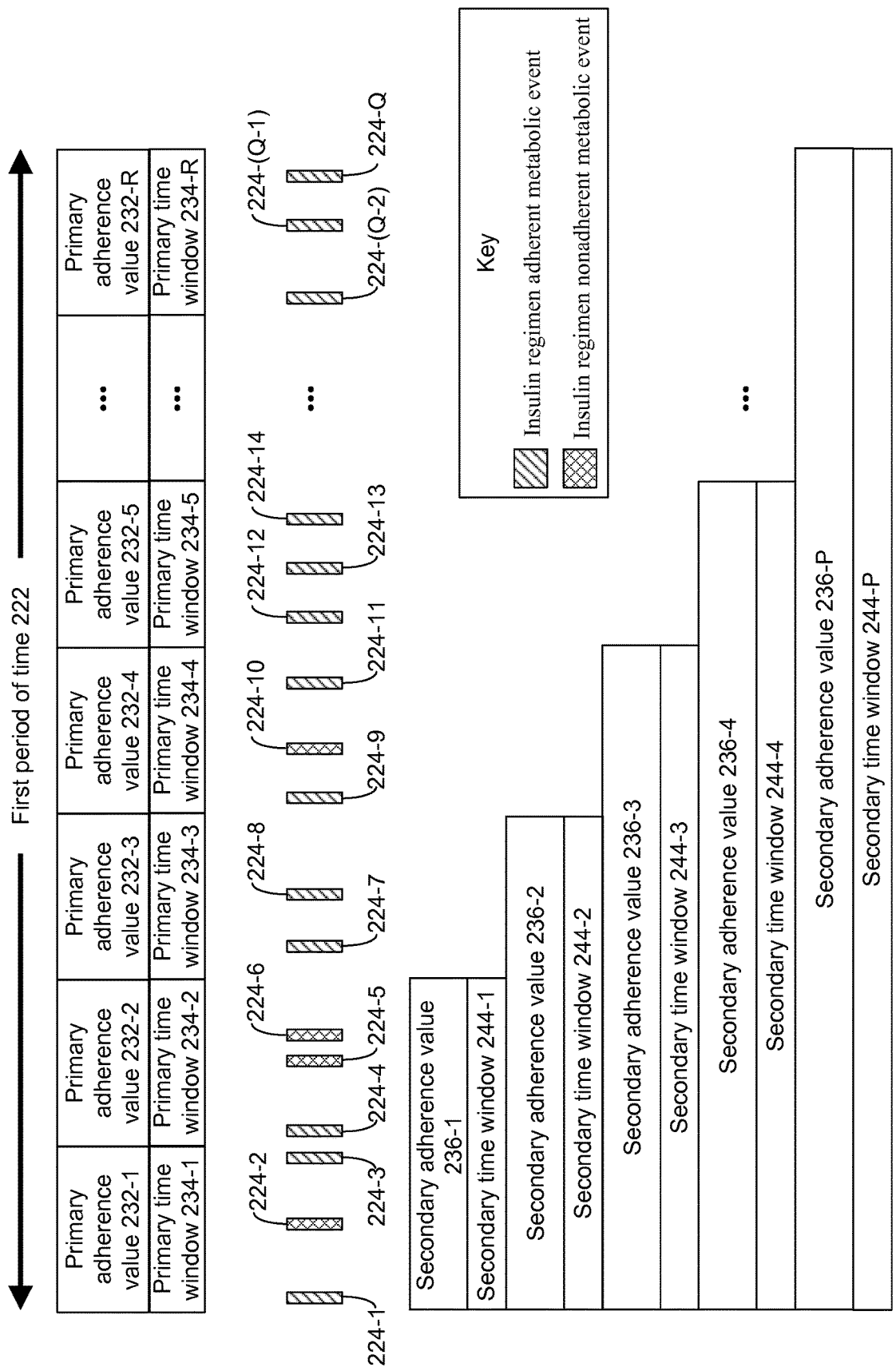
FIG. 13 illustrates the temporal relationship between primary adherence values, primary time windows, metabolic events, secondary adherence values and secondary time windows in an embodiment where each primary time window has a duration of one day, and each respective secondary time window represents a running average from the beginning of a first time period in accordance with an embodiment of the present disclosure.

Referring to block 416 of FIG. 4B, in some embodiments, each metabolic event 224 in the plurality of metabolic events is a meal event and the insulin medicament dosage regimen 206 is a bolus insulin medicament dosage regimen 214. Referring to block 418 of FIG. 4B, in some such embodiments, the first fixed duration of each primary time window 234 is a day, and each respective secondary time window 244 in the plurality of secondary time windows represents a running average from the beginning of the first time period. FIG. 13 illustrates. In FIG. 13, each primary time window 234 is a day, and each respective secondary time window 244 in the plurality of secondary time windows represents a running average from the beginning of the first time period. Thus, for example the secondary adherence value 236-P of FIG. 13 is calculated by dividing the number of regimen compliant metabolic events in the first period of time 222 {224-1, 224-3, 224-4, 224-7, 224-8, 224-9, 224-11, 224-12, 224-13, 224-14, . . . , 224-(zQ-2), 224-(Q-1), 224-Q} by the total number of regimen metabolic events in the first time period (Q).

Referring to block 420 of FIG. 4B, in some embodiments, respective metabolic events 224 in the plurality of metabolic events that occur earlier than a set cutoff time are downweighted relative to respective metabolic events in the plurality of metabolic events that occur after the set cutoff time in each respective primary time window.

In some embodiments, the application of the set cutoff time is applied to the computation the primary adherence values 232 and not the secondary adherence values 242.

In some embodiments, the application of the set cutoff time is applied to the computation of both the primary adherence values 232 and the secondary adherence values 242.

Figure 14:
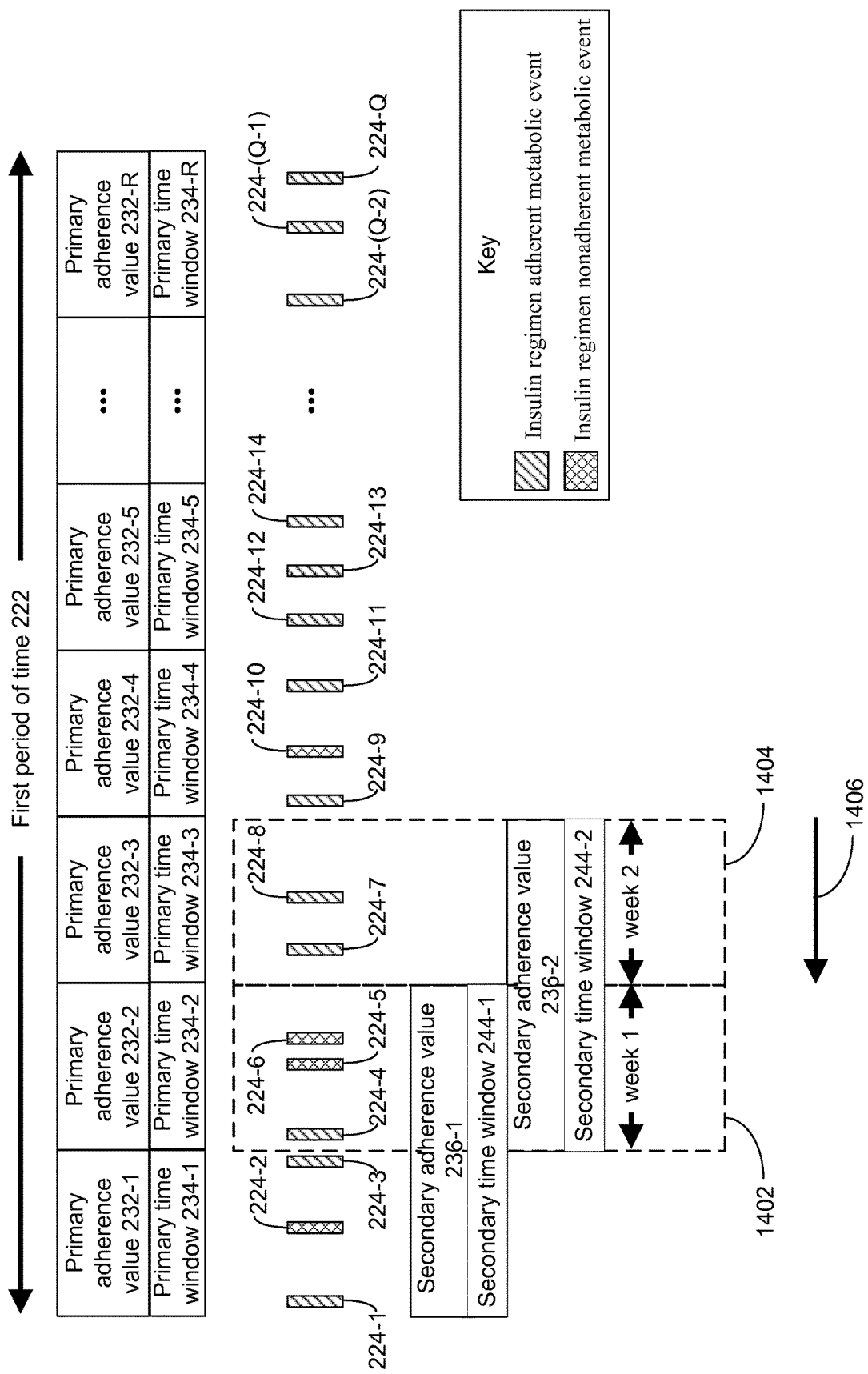
FIG. 14 illustrates the temporal relationship between primary adherence values, primary time windows, metabolic events, secondary adherence values and secondary time windows where each primary time window has a duration of one week, each secondary time window has a duration of two weeks, and metabolic events that occur earlier than a set cutoff time are down-weighted relative to metabolic events that occur after the set cutoff time in the secondary time windows in accordance with an embodiment of the present disclosure.

In some embodiments, the application of the set cutoff time is applied only to the computation of the secondary adherence values 242, not the primary adherence values 232. In such embodiments, the primary adherence values 232 are computed as described above whereas the secondary adherence values 242 are computed by taking the cutoff time into consideration. To illustrate, referring to FIG. 6, when the set cutoff time is one week and the first fixed duration of the primary time window is one week, whereas the secondary time window 244 is set for two weeks, such downweighting will only affect computation of the secondary adherence values, not the primary adherence values. This is because the cutoff time is applied retrospectively from the end of each primary and/or secondary time window. FIG. 14 illustrates. In the example illustrated in FIG. 14, the secondary time window 244-2 has a duration of two weeks, the primary time window has a duration of one week, and the set cutoff time is one week, applied retrospectively from the end of time window 244-2 as illustrated by arrow 1406. Thus, in computation of the secondary adherence value 236-2, metabolic events 224-4 through 224-6 are downweighted relative to metabolic events 224-7 and 224-8. Without the downweighting, the secondary adherence value is computed as the division of the number of adherent metabolic events (3: 224-4, 224-5, and 224-7) by the total number of metabolic events (5: 224-4 through 224-8) or 3/5. With the set cutoff time of one week, metabolic events in week 1, within box 1402 of FIG. 14, are downweighted relative to the metabolic events in week 2, within box 1404 of FIG. 14.

Downweighting is particularly useful in the example of FIG. 13, where each respective secondary time window 244 in the plurality of secondary time windows represents a running average from the beginning of the first time period. In such embodiments, it is useful to downweight, or even disregard, older metabolic events when computing the secondary adherence values. This could be done by a linear function of time, a non-linear function of time, or a memory cut-off where data older than a specific time period are completely eliminated. In one example, linear weighing of adherence data when calculating a 12 week secondary adherence value could be done by the following calculation:

$$12 \text{ week linear adherence} = \frac{1}{\sum w} \sum_{i=1}^{12} w_i (\text{Weekly adherence})_i$$

where, $$\overline{w} = \{w_1, w_2 \ldots, w_{12}\} = \left\{\frac{12}{12}, \frac{11}{12}, \frac{10}{12}, \ldots, \frac{1}{12}\right\}.$$

An example of this is illustrated for the secondary adherence values plotted as line 806 in FIG. 8B using as input the secondary time windows illustrated in FIG. 13, whereas as line 802 is weekly primary adherence values.

An example of a non-linear weighting could be, for example, weighing the metabolic events in the last four weeks 100%, the four previous weeks 50%, and disregarding all metabolic events older than eight weeks when computing a respective adherence value. Such an example is illustrated for the secondary adherence values plotted as line 808 in FIG. 8C using as input the secondary time windows illustrated in FIG. 13, whereas as line 802 is weekly primary adherence values.

The extent that metabolic events that are occur prior to a set cutoff time used for downweighting is application dependent. In some embodiments, such metabolic events are uniformly downweighted by a predetermined amount between zero and 99 percent, such as fifty percent. Thus, in an example of FIG. 14 where the downweight is fifty percent, metabolic events 224-4 through 224-6 are downweighted by fifty percent and the secondary adherence value 236-2 is computed as (0.5+1.0+1.0)/(0.5+0.5+0.5+1+1) for the division of metabolic events 224-4, 224-7 and 224-8 by metabolic events 224-4 through 224-8. In an example of FIG. 14 where the downweight is seventy five percent, metabolic events 224-4 through 224-6 are downweighted by seventy five percent and the secondary adherence value 236-2 is computed as (0.25+1.0+1.0)/(0.25+0.25+0.25+1+1) for the division of metabolic events 224-4, 224-7 and 224-8 by metabolic events 224-4 through 224-8. In an example of FIG. 14 where the downweight is ninety percent, metabolic events 224-4 through 224-6 are downweighted by ninety percent and the secondary adherence value 236-2 is computed as (0.10+1.0+1.0)/(0.10+0.10+0.10+1+1) for the division of metabolic events 224-4, 224-7 and 224-8 by metabolic events 224-4 through 224-8.

In some embodiments, metabolic events occurring before the set cutoff time are downweighted as a function of time, so that events occurring earlier in time than later events are downweighted more. Referring to FIG. 14 in such an example, metabolic event 224-4 would be downweighted more than metabolic event 224-5 which, in turn, would be downweighted more than metabolic event 224-5, whereas metabolic events 224-7 and 224-8 would each have full value.

Referring to block 422 of FIG. 4B, in some embodiments, respective metabolic events in the plurality of metabolic events are down-weighted as a linear function of time in each respective primary time window. For instance, referring to FIG. 6, metabolic event 224-1 would be downweighted more than metabolic event 224-2 which, in turn, would be downweighted more than metabolic event 224-3 and the extent of such downweighting would be a linear function of time. In some embodiments, respective metabolic events in the plurality of metabolic events are down-weighted as a linear function of time in each respective primary time window and/or secondary time window.

Referring to block 424 of FIG. 4B, in some embodiments, the first plurality of adherence values or the second plurality of adherence values are analyzed for a drop off in adherence.

Figure 10:
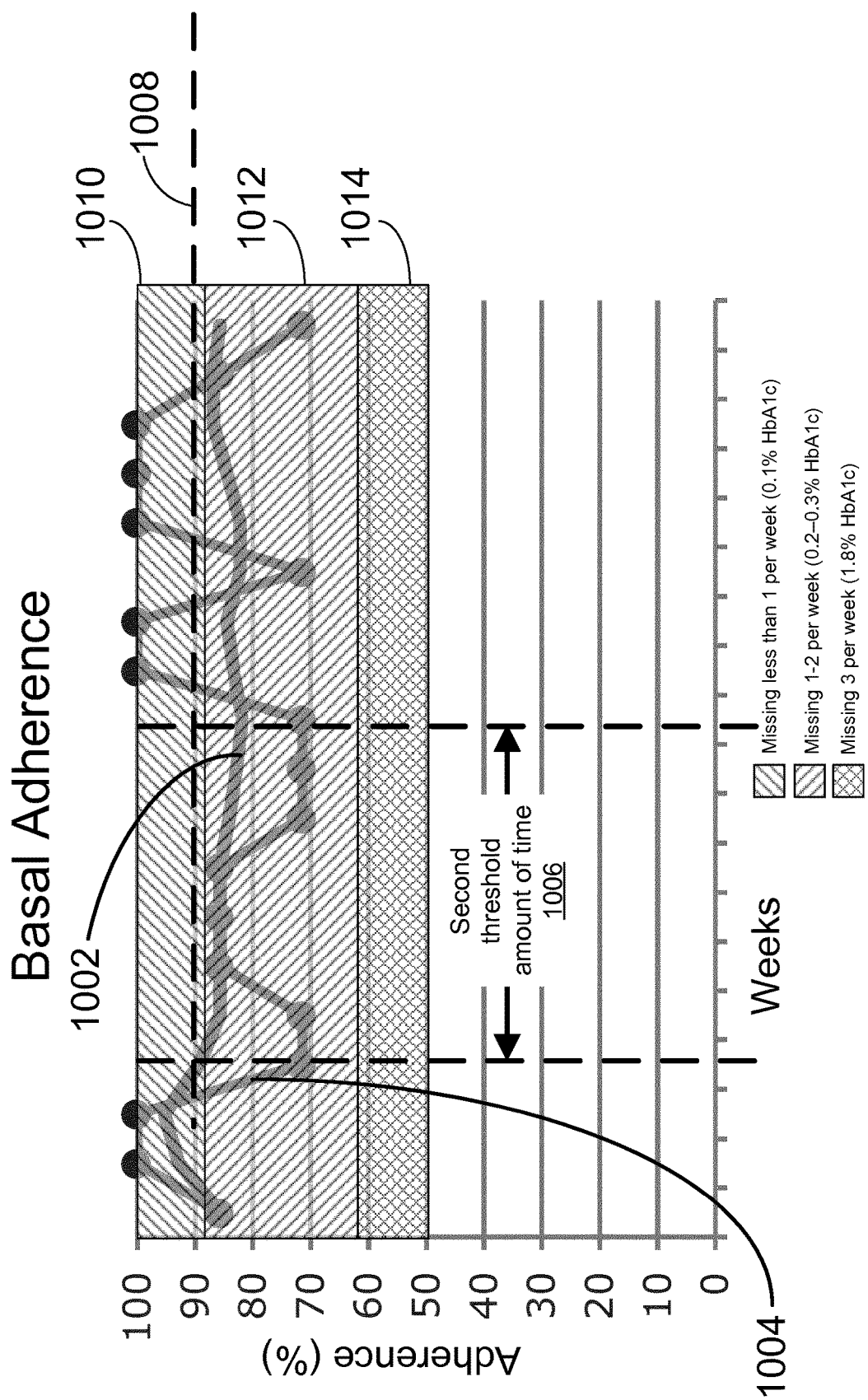
FIG. 10 illustrates an example of how the adherence effect on HbA1c, for basal regimen adherence data, is communicated in accordance with an embodiment of the present disclosure.

In some such embodiments, such a trend is identified as a drop off below a first threshold adherence value for at least a second threshold amount of time. FIG. 10 illustrates a drop off below a first threshold adherence value for at least a second threshold amount of time.

In some such embodiments, when such a trend is identified, insulin medicament dosage in the insulin medicament dosage regimen for the subject is reduced. In other words, when it is determined that the subject is not adhering to the insulin regimen, the insulin regimen is shifted to a more conservative regimen to protect the subject from adverse events. Values for the first threshold adherence value and the second threshold amount of time are highly application dependent and will depend on a number of factors such as health care practitioner judgment, stage of the underlying diabetic condition, additional complications in the subject's health, and type of insulin medicaments the subject is taking. In general the second threshold amount of time is on the order of weeks or months to ensure that a change in treatment regimen is warranted.

Figure 9:
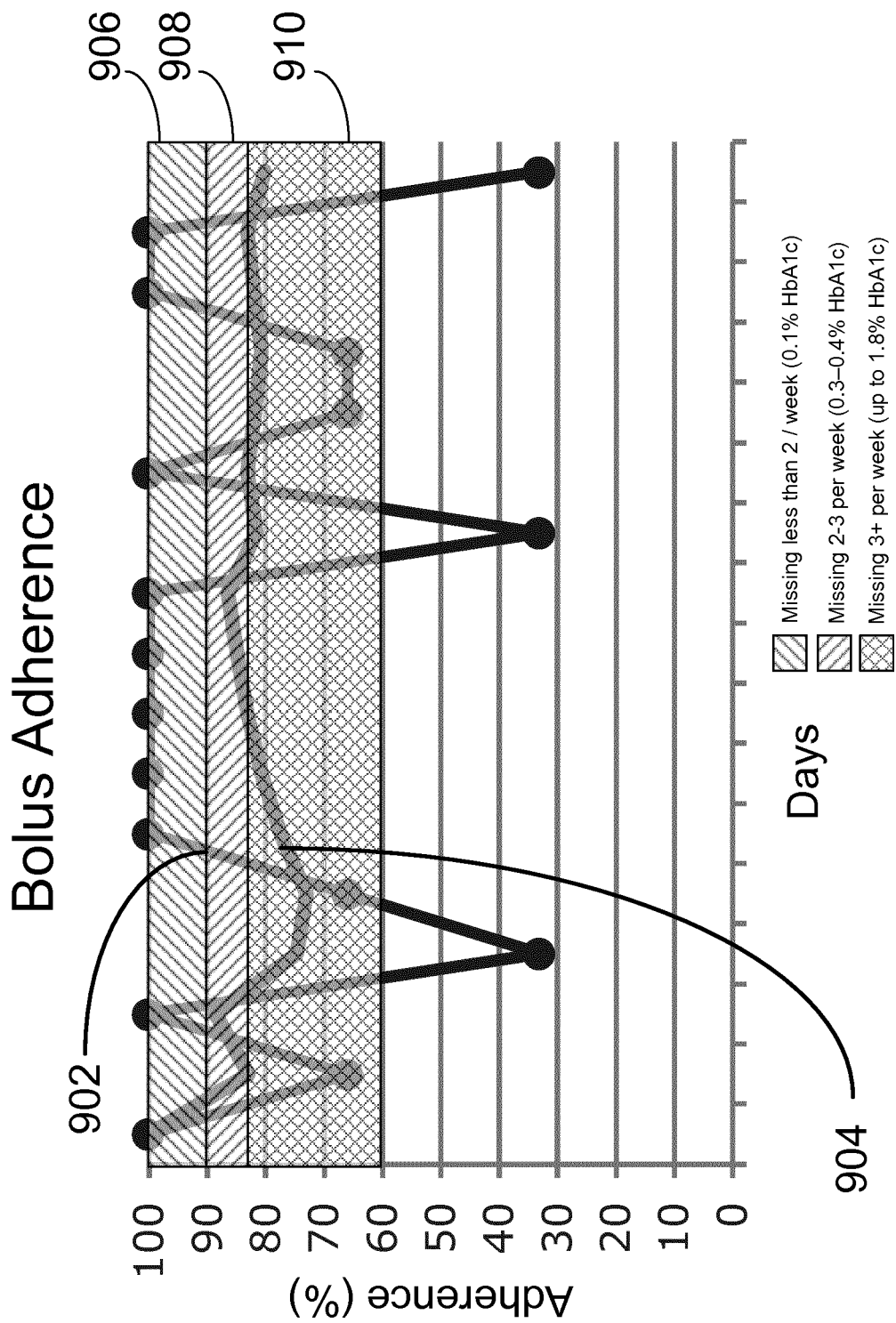
FIG. 9 illustrates an example of how the adherence effect on HbA1c, for bolus regimen adherence data, is communicated in accordance with an embodiment of the present disclosure.

Referring to block 426 of FIG. 4B, in some embodiments a HbA1c lookup table 238 is obtained that includes a calculated HbA1c increase as a function of adherence values in the first plurality of adherence values. For instance, the methods disclosed in Poulsen and Randløv, 2009, "How Much Do Forgotten Insulin Injections Matter to Hemoglobin A1c in People with Diabetes? A Simulation Study," Journal of Diabetes Science and Technology Mar; 2(2):229-235, which is hereby incorporated by reference are used determine how a missed dose affects HbA1c level. The referenced study estimates that forgetting 2.1 bolus injections per week results in an approximate 0.3 to 0.4 percent increase in HbA1c, and forgetting the same amount of basal injections (assuming a dosage regimen requiring 2 basals per day) results in a 0.2 to 0.3 percent rise in HbA1c levels. Furthermore, the reference estimate that forgetting 39% of the basal or bolus injections results in as much as a 1.8 percent increase in HbA1c. Such numbers can be used to estimate how much nonadherence is affecting the patient's treatment outcome. FIG. 9 illustrates the example of forgetting 2.1 bolus insulin injections for week according to the following calculations:

$$\text{Boluses to take: } \frac{7 \text{ days}}{\text{week}} * \frac{3 \text{ boluses}}{\text{day}} = \frac{21 \text{ boluses}}{\text{week}}$$

$$\text{Forgetting 2.1 boluses/week corresponds to: } \frac{18.9}{21} = 90\% \text{ adherence.}$$

Hence, adherence around 90% increases HbA1c about 0.3-0.4%, and adherence around 60% results in 1.8% increase in HbA1c. The same can be done for basal adherence.

Further, an indication of which of the primary adherence values in the plurality of primary adherence values cause the calculated HbA1c increase to be over a threshold value according to the HbA1c lookup table is communicated. FIG. 9 illustrates this feature for adherence to a bolus insulin medicament dosage regimen, where the HbA1c lookup table 238 indicates that a bolus regimen adherence of between 90 percent and 100 percent (e.g., missing less than 2 bolus injections per week) can cause an increase in about 0.1% HbA1c 906 for the subject, a bolus regimen adherence of between 82 percent and 90 percent (e.g., missing 2-3 bolus injections per week) can cause an increase in about 0.3% to 0.4% HbA1c 908 for the subject, and a bolus regimen adherence of between 60 percent and 82 percent (e.g., missing more than three bolus injections per week) can cause an increase in about 1.8% HbA1c 910 for the subject. From FIG. 9 it can be seen which metabolic events are responsible for which increases in HbA1c. For instance, the metabolic events occurring when lines 902 and/or 904 fall into zone 910 are causing an increase of 1.8 percent HbA1c.

FIG. 9 expresses adherence in terms of missed bolus injections per week. However, bolus injections are temporally matched to metabolic events (e.g., meal events) in order to provide a characterization 228 to such metabolic events in some embodiments of the first data set 210. Thus, in some such embodiments, adherence is equivalently expressed in terms of percentage of noncompliant metabolic events 224.

FIG. 10 illustrates the feature for adherence to a basal insulin medicament dosage regimen 208, where the HbA1c lookup table 238 indicates that a basal regimen adherence of between 88 percent and 100 percent (e.g., missing less than one basal injection per week) can cause an increase in about 0.1% HbA1c 1010 for the subject, a basal regimen adherence of between 62 percent and 88 percent (e.g., missing 1-2 basal injections per week) can cause an increase in about 0.2% to 0.3% HbA1c 1012 for the subject, and a basal regimen adherence of between 50 percent and 62 percent (e.g., missing three basal injections per week) can cause an increase in about 1.8% HbA1c 1012 for the subject. From FIG. 10 it can be seen which metabolic events are responsible for which increases in HbA1c. For instance, the metabolic events occurring when lines 1002 and/or 1004 fall into zone 1012 are causing an increase of 0.2 to 0.3 percent HbA1c.

FIG. 10 expresses adherence in terms of missed basal injections per week. However, because basal injections are temporally matched to metabolic events (e.g., fasting events) in order to provide a characterization 228 to such metabolic events in some embodiments of the first data set 210, in some such embodiments, adherence is equivalently expressed in terms of percentage of noncompliant metabolic events 224.

Referring to block 428 of FIG. 4C, advantageously, the plurality of primary adherence values across the first period of time and/or the superposition of the plurality of primary adherence values and the plurality of secondary adherence values across the first period of time can be communicated to a monitor device 250 that is mobile to thereby monitor adherence to a prescribed insulin medicament dosage regimen for the subject over time.

Thus, in some embodiments, monitor device 250 is a mobile device that includes a display 208 and the communication of the adherence values includes presenting them on the display. FIGS. 11 and 12 illustrate this feature for bolus adherence and basal adherence respectively.

Referring to block 430 of FIG. 4C, in some embodiments a second data set 240 is obtained. The second data set comprises a plurality of autonomous glucose measurements of the subject and, for each respective autonomous glucose measurement 242 in the plurality of autonomous glucose measurements, a timestamp 244 representing when the respective measurement was made. In some such embodiments, these glucose measurements are temporally matched to the plurality of primary adherence values and/or primary secondary adherence values over time within the first period of time and the glucose measurements superimposed onto the primary adherence values and/or primary secondary adherence values are displayed on the monitor device 250 so that the subject can get a sense of how adherence affects glucose values in real time. Referring to block 432 of FIG. 4C, in some such embodiments, the adherence device 250 comprises a wireless receiver 284 to receive the second data set wirelessly from a glucose sensor 102 affixed to the subject.

Example 1: Use of autonomous glucose measurements to identify metabolic events and to characterize them as insulin regimen adherent or insulin regimen nonadherent. Block 402 above described how a second data set 240 comprising a plurality of glucose measurements is obtained autonomously in some embodiments. In this example, in addition to the autonomous glucose measurements, insulin administration events are obtained in the form of insulin medicament records from one or more insulin pens and/or pumps 104 used by the subject to apply the prescribed insulin regimen. These insulin medicament records may be in any format, and in fact may be spread across multiple files or data structures. As such, in some embodiments, the instant disclosure leverages the recent advances of insulin administration pens, which have become "smart" in the sense that they can remember the timing and the amount of insulin medicament administered in the past. One example of such an insulin pen 104 is the NovoPen 5. Such pens assists patients in logging doses and prevent double dosing. It is contemplated that insulin pens will be able to send and receive insulin medicament dose volume and timing, thus allowing the integration of continuous glucose monitors 102, insulin pens 104 and the algorithms of the present disclosure. As such, insulin medicament records from one or more insulin pens 104 and/or pumps is contemplated, including the wireless acquisition of such data from the one or more insulin pens 104.

In some embodiments, each insulin medicament record comprises: (i) a respective insulin medicament injection event including an amount of insulin medicament injected into the subject using a respective insulin pen in the one or more insulin pens and (ii) a corresponding electronic timestamp that is automatically generated by the respective insulin pen 104 upon occurrence of the respective insulin medicament injection event.

In some embodiments, a plurality of fasting events, which is one form of metabolic event 224, are identified using the autonomous glucose measurements 242 of the subject and their associated glucose measurement timestamps 244 in the second data set 240. Glucose measurements during fasting events are of importance for measuring basal glucose levels, i.e, the glucose level related to the basal injection events. The basal glucose level allows evaluation of the effect of the basal injection event.

There are a number of methods for detecting a fasting event using autonomous glucose measurements 242 from a glucose monitor 102. For instance, in some embodiments a first fasting event (in the plurality of fasting events) is identified in a first time period (e.g., a period of 24 hours) encompassed by the plurality of autonomous glucose measurements by first computing a moving period of variance $\sigma_k^2$ across the plurality of autonomous glucose measurements, where:

$$\sigma_k^2 = \left(\frac{1}{M} \sum_{i=k-M}^{k} (G_i - \overline{G})\right)^2$$

and where, $G_i$ is the $i^{th}$ glucose measurement in the portion k of the plurality of glucose measurements, M is a number of glucose measurements in the plurality of glucose measurements and represents a contiguous predetermined time span, $\overline{G}$ is the mean of the M glucose measurements selected from the plurality of glucose measurements, and k is within the first time period. As an example, the glucose measurements may span several days or weeks, with autonomous glucose measurements taken every five minutes. A first time period k (e.g., one day) within this overall time span is selected and thus the portion k of the plurality of measurements is examined for a period of minimum variance. The first fasting period is deemed to be the period of minimum variance $\min_k \sigma_k^2$ within the first time period. Next, the process is repeated with portion k of the plurality of glucose measurements by examining the next portion k of the plurality of glucose measurements for another period of minimum variance thereby assigning another fasting period. Repetition of this method through all portions k of the plurality of glucose measurements is used to build the plurality of fasting periods.

Once the fasting events are identified, by the method described above or any other method, a first characterization 228 is applied to each respective fasting event in the plurality of identified fasting events. Thus, for each respective fasting event there is a first characterization 228 for the respective fasting event. The first characterization is one of insulin regimen adherent and insulin regimen nonadherent. More specifically, here, the first characterization is one of basal insulin regimen adherent and basal insulin regimen nonadherent.

A respective fasting event is deemed basal insulin regimen adherent when the acquired one or more medicament records establish, on a temporal and quantitative basis, adherence with the prescribed basal insulin medicament dosage regimen during the respective fasting event. A respective fasting event is deemed basal regimen nonadherent when the acquired one or more medicament records do not include one or more medicament records that establish, on a temporal and quantitative basis, adherence with the prescribed basal insulin medicament dosage regimen during the respective fasting event. In some embodiments the basal regimen 208 specifies that a basal dose of long acting insulin medicament 210 is to be taken during each respective epoch 212 in a plurality of epochs and that a respective fasting event is deemed basal insulin medicament regimen 208 nonadherent when there are no medicament records for the epoch 212 associated with the respective fasting event. In various embodiments, each epoch in the plurality of epochs is two days or less, one day or less, or 12 hours or less 418. Thus, consider the case where the second data set 240 is used to identify a fasting period and the prescribed basal insulin medicament dosage regimen 208 specifies to take dosage A of a long acting insulin medicament 210 every 24 hours. In this example, therefore, the epoch is one day (24 hours). The fasting event is inherently timestamped because it is derived from a period of minimum variance in timestamped glucose measurements, or by other forms of analysis of the timestamped autonomous glucose measurements. Thus the timestamp, or period of fasting, represented by a respective fasting event is used as a starting point for examining whether the fasting event is basal insulin medicament regimen adherent. For instance, if the period of fasting associated with the respective timestamp is 6:00 AM on Tuesday, May 17, what is sought in the medicament injection records is evidence that the subject took dosage A of the long acting insulin medicament in the 24 hour period (the epoch) leading up to 6:00 AM on Tuesday, May 17 (and not more or less of the prescribed dosage). If the subject took the prescribed dosage of the long acting insulin medicament during this epoch, the respective fasting event (and/or the basal injection event and/or the glucose measurements during this time) is deemed basal regimen adherent. If the subject did not take the prescribed dosage of the long acting insulin medicament 210 during this epoch 212 (or took more than the prescribed dosage of the long acting insulin medicament during this period), the respective fasting event (and/or the basal injection event and/or the glucose measurements during this time) is deemed basal regimen nonadherent.

While the use of the fasting event to retrospectively determine whether a basal injection event is basal insulin medicament regimen adherent has been described, the present disclosure is not so limited. In some embodiments, the epoch is defined by the basal insulin medicament regimen and, so long as the subject took the amount of basal insulin required by the basal regimen during the epoch (and not more), even if after the fasting event, the fasting event will be deemed basal insulin medicament regimen adherent. For instance, if the epoch is one day beginning each day at just after midnight (in other words the basal regimen specifies one or more basal insulin medicament dosages to be taken each day, and further defines a day as beginning and ending at midnight), and the fasting event occurs at noon, the fasting event will be deemed compliant provided that the subject takes the basal injections prescribed for the day at some point during the day.

In some embodiments a fasting event is not detected during an epoch when, in fact, the basal insulin medicament regimen specifies that a basal insulin injection event must occur. Thus, the basal injection should be taken according to the prescribed basal insulin medicament regimen 208. According to the above use case, this epoch would not have a basal adherence categorization for failure to find a fasting event. In some such embodiments, because the basal insulin medicament dosage regimen 208 is known, a determination as to the adherence (of the glucose measurement during the epoch in question and/or the basal injection event in the epoch) is based on the basal insulin medicament regimen itself and the injection event data, and thus does not require detecting the fasting period from the injection event data. As another example, if the basal insulin medicament regimen is once weekly basal injection, the exemplary procedure would look for a basal injection within a seven day window even if a fasting event is not found.

In some embodiments, the prescribed insulin medicament dosage regimen 206 further comprises a bolus insulin medicament dosage regimen 214 in addition to or instead of the basal insulin medicament dosage regimen 208.

In embodiments where the subject is taking more than one insulin medication type, each respective insulin medicament injection event in the plurality of medicament records provides a respective type of insulin medicament injected into the subject from one of (i) a long acting insulin medicament and (ii) a short acting insulin medicament. Typically, the long acting insulin medicament is for a basal insulin medicament dosage regimen 208 whereas the short acting insulin medicament is for a bolus insulin medicament dosage regimen 214.

Thus, advantageously, the instant disclosure can also make use of the bolus insulin medicament injection events, when such events are available, to provide an additional type of categorized metabolic event 224 in the first data set 220. In some such embodiments, the bolus insulin medicament injection events are made use of in the following way. A plurality of meal events are identified using the plurality of autonomous glucose measurements 242 and the corresponding timestamps 244 in the second data set 240 using a meal detection algorithm. If no meal is detected, the process ends. If a meal is detected then a characterization is applied to the respective meal event. In this way, a plurality of meal events, with each respective meal event including a characterization that is one of "bolus regimen adherent" and "bolus regimen nonadherent" is acquired. Such information can then be used in the systems and methods of the present disclosure, where each meal is considered a metabolic event 224 and the characterization of such meals as "bolus regimen adherent" and "bolus regimen nonadherent" is the characterization 228 of the metabolic event.

In some embodiments, a respective meal is deemed bolus regimen adherent when one or more medicament records in the plurality of medicament records indicates, on a temporal basis, a quantitative basis and a type of insulin medicament basis, adherence with the bolus insulin medicament dosage regimen 214 during the respective meal. In some embodiments, a respective meal is deemed bolus regimen nonadherent when the plurality of medicament records fails to indicate adherence, on a temporal basis, a quantitative basis, and a type of insulin medicament basis, with the standing bolus insulin medicament dosage regimen during the respective meal 608. For instance, consider the case where the standing bolus insulin medicament dosage regimen specifies that dosage A of insulin medicament B is to be taken up 30 minutes before a respective meal and that a certain meal that occurred at 7:00 AM on Tuesday, May 17. It will be appreciated that dosage A may be a function of the anticipated size or type of meal. What is sought in the medicament records is evidence that the subject took dosage A of insulin medicament B in the 30 minutes leading up to 7:00 AM on Tuesday, May 17 (and not more or less of the prescribed dosage). If the subject took the prescribed dosage A of the insulin medicament B during the 30 minutes leading up to the respective meal, the respective meal (and/or the bolus administration(s) and/or the glucose measurements during this time) is deemed bolus regimen adherent. If the subject did not take the prescribed dosage A of the insulin medicament B during the 30 minutes leading up to the respective meal (or took more than the prescribed dosage A of the insulin medicament B during this period), the respective meal (and/or the bolus administration and/or the glucose measurements during this time) is deemed bolus regimen nonadherent. The time period of 30 minutes here is exemplary, in other embodiments the time is shorter or longer (e.g., between 15 minutes to 2 hours prior to the meal and/or is dependent upon the type of insulin medicament prescribed).

In some embodiments the characterization of a metabolic event as insulin regimen adherent can be determined as a degree or percentage of insulin regimen adherent depending on the estimated glycemic effect of taking a dose later than recommended or taking an amount of dose below or above a recommended dose.

In some embodiments, a plurality of feed-forward events are acquired and used to help characterize metabolic events. In some embodiments, each respective feed-forward event represents an instance where the subject has indicated they are having or are about to have a meal. In such embodiments, the plurality of meal events determined using the autonomous glucose measurements 242 are verified against the plurality of feed-forward events by either removing any respective meal event in the plurality of meal events that fails to temporally match any feed-forward event in the plurality of feed-forward events.

In some embodiments, the bolus insulin medicament dosage regimen 214 specifies that the short acting insulin medicament is to be taken up to a predetermined amount of time prior to a meal. In some such embodiments, a respective meal is deemed bolus regimen nonadherent when there is no insulin medicament record of the short acting insulin medicament type having an electronic timestamp up to the predetermined amount of time prior to the respective meal. In some such embodiments, the predetermined amount of time is thirty minutes or less, twenty minutes or less, or fifteen minutes or less.

In some embodiments, the long acting insulin medicament consists of a single insulin medicament having a duration of action that is between 12 and 24 hours or a mixture of insulin medicaments that collectively have a duration of action that is between 12 and 24 hours. Examples of such long acting insulin medicaments include, but are not limited to Insulin Degludec (developed by NOVO NORDISK under the brand name Tresiba), NPH (Schmid, 2007, "New options in insulin therapy. J Pediatria (Rio J). 83(Suppl 5):S146-S155), Glargine (LANTUS, Mar. 2, 2007, insulin glargine [rDNA origin] injection, [prescribing information], Bridgewater, N.J.: Sanofi-Aventis), and Determir (Plank et al., 2005, "A double-blind, randomized, doseresponse study investigating the pharmacodynamic and pharmacokinetic properties of the long-acting insulin analog detemir," Diabetes Care 28:1107-1112).

In some embodiments, the short acting insulin medicament consists of a single insulin medicament having a duration of action that is between three to eight hours or a mixture of insulin medicaments that collectively have a duration of action that is between three to eight hours. Examples of such short acting insulin medicaments include, but are not limited, to Lispro (HUMALOG, May 18, 2001, insulin lispro [rDNA origin] injection, [prescribing information], Indianapolis, Ind.: Eli Lilly and Company), Aspart (NOVOLOG, July 2011, insulin aspart [rDNA origin] injection, [prescribing information], Princeton, N.J., NOVO NORDISK Inc., July, 2011), Glulisine (Helms Kelley, 2009, "Insulin glulisine: an evaluation of its pharmacodynamic properties and clinical application," Ann Pharmacother 43:658-668), and Regular (Gerich, 2002, "Novel insulins: expanding options in diabetes management," Am J Med. 113:308-316).

In some embodiments, the identification of the plurality of meal events from the autonomous glucose measurements 242 in the second data set 240 is performed by computing: (i) a first model comprising a backward difference estimate of glucose rate of change using the plurality of autonomous glucose measurements, (ii) a second model comprising a backward difference estimate of glucose rate of change based on Kalman filtered estimates of glucose using the plurality of autonomous glucose measurements, (iii) a third model comprising a Kalman filtered estimate of glucose and Kalman filtered estimate of rate of change (ROC) of glucose based on the plurality of autonomous glucose measurements, and/or (iv) a fourth model comprising a Kalman filtered estimate of rate of change of ROC of glucose based on the plurality of autonomous glucose measurements. In some such embodiments, the first model, the second model, the third model and the fourth model are each computed across the plurality of autonomous glucose measurements and each respective meal event in the plurality of meal events is identified at an instance where at least three of the four models indicate a meal event. For further disclosure on such meal event detection, see Dassau et al., 2008, "Detection of a Meal Using Continuous Glucose Monitoring," Diabetes Care 31, pp. 295-300, which is hereby incorporated by reference. See also, Cameron et al., 2009, "Probabilistic Evolving Meal Detection and Estimation of Meal Total Glucose Appearance," Journal of Diabetes Science and Technology 3(5), pp. 1022-1030, which is hereby incorporated by reference.

Example 2. The following example works through how primary adherence values 232 are reported for various basal insulin medicament dosage regimens 208. First, consider a prescribed basal insulin dosage medicament regimen 208 consisting of two basal injections per twenty four hours. In some embodiments, the duration of the primary time window 234 is set at 24 hours, though in other embodiments the duration of the primary time window 234 is set at some multiple of 24 hours, such as every two days, every three days, and so forth. If the duration of the primary time window 234 is set to 24 hours, the number of metabolic events 224 in a given primary time window 234 is one, a single fasting event. If two basal injections are registered in a given primary time window 234, the injections are deemed adherent and/or the fasting event is deemed adherent. If one or zero injections are registered, the fasting event is nonadherent. In this example, each primary adherence value 232 for the basal insulin medicament dosage regimen adherence is categorized based on fasting events. There is a single fasting event per day, and each such fasting event is independently categorized.

Thus, in the scenario of one fasting event per day, a dosage regimen of two basal injections per day, and a primary time window 234 length of 1 day, each fasting event is categorized as either regimen adherent or regimen nonadherent based on whether there have been two injections in the past 24 hours. In accordance with the present disclosure, the first data set 220 provides a stream of time stamped metabolic events {$M_1, \ldots, M_N$}, over a first period of time. This stream of events is used to compute respective primary adherence values 232 for corresponding primary time windows 234, with each such primary adherence value 232 representing a corresponding primary time window 234 in the first period of time 222 represented by the first data set 220. There is no requirement that the length of primary time window be dictated by the basal dosing regimen. That is, the duration of the primary window can be a day, a week, a month, or three months. When the duration of the primary time window is chosen to be a day, then the primary adherence value 232 for the primary time window 234 will be one of two values: 0 (the fasting event of that day is regimen nonadherent) or 1 (the fasting event of that day was regimen adherent). That is, the computed primary adherence value 232 for the primary time window 234 will be a number that is zero or one.

In some embodiments primary adherence values 232 and/or secondary adherence values 244 are scaled so that they fall into a range other than zero to 1, such as zero to 100, zero to 1000 or any other suitable scale.

In the scenario of a single fasting event per day, a dosage regimen of two basal injections per day, and a primary time window length of 1 week, each fasting event is categorized as either regimen adherent or regimen nonadherent based on whether there have been two injections in the past 24 hours. With the primary time window 234 duration set at one week, then the primary adherence value will be one of eight values: 0/7 (regimen nonadherent on all seven days), 1/7 (one fasting event in one day was regimen adherent, six other days were regimen nonadherent), 2/7 (fasting event in each of two days are regimen adherent, five other days were regimen nonadherent), . . . , 7/7 (regimen adherent on all seven days). Thus, the primary adherence value is one of 8 values that range between zero and one. In some embodiments these primary adherence values 232 are then scaled so that they fall into a range other than zero to 1, such as zero to 100, zero to 1000 or any other suitable scale.

Next, consider a basal insulin medicament dosage regimen 208 that specifies one basal injection per week. There is one fasting event per day, and each such fasting event is categorized independently. Each respective fasting event is categorized as regimen adherent or regimen nonadherent based on whether there has been an injection in the week prior to the respective fasting event. Thus, a stream of time stamped metabolic events {$M_1, \ldots, M_N$}, over a first period of time, is obtained in the form of the first data set 220. This stream of events is then used to compute a plurality of primary adherence values, with each such primary adherence value representing a primary time window 234 in the first period. There is no requirement that the duration of the primary time window 234 be dictated by the basal dosing regimen. That is, here, the duration of the primary time window can be a week, a month, three months, or any other suitable period of time. In fact, the duration of the primary time window could be one day, since each metabolic event (here, a fasting event) is independently categorized.

If the duration of the primary time window 234 is set to 24 hours, then each primary adherence value 234 for respective primary time window 234 will be one of two values: "0" (the fasting event of that day was regimen nonadherent) or "1" (the fasting event of that day was regimen adherent). That is, the computed primary adherence value 234 for the corresponding primary time window 234 will be a number that ranges between zero and one. In some embodiments, the duration of the primary time window 234 will be chosen to be one week or longer for more of a gradient between zero and one. This primary adherence value could be multiplied by the number of metabolic events in the primary time window or some other scalar for purposes of conveying information regarding the status of the subject's health.

Example 3. The following example works through how primary adherence values 232 are reported for various bolus insulin medicament dosage regimens 214. In particular, consider a prescribed bolus regimen that is one bolus injection for each ingested meal and the duration of the primary time window 234 is four hours. Here, bolus regimen adherence is determined based upon metabolic events that are meal events. There may be three meal events per day, and each such metabolic event is separately characterized.

In the case of three meal events per day and a regimen that specifies a bolus injection before each meal, each meal event is characterized as either regimen adherent or regimen nonadherent based on whether there has been a bolus injection prior to that meal within a predetermined amount of time. Thus, a stream of time stamped metabolic events {$M_1, \ldots, M_N$} over a first period of time, is obtained in the form of the first data set 220. This stream of events is then used to compute a plurality of primary adherence values, with each such primary adherence value 232 representing a corresponding primary time window 234 in the first period of time 222. There is no requirement that the duration of the primary time window 234 be dictated by the timing of injection events in the bolus dosing regimen. That is, the duration of the primary time window can be a day, a week, a month, or three months, or any other suitable amount of time. If the duration of the primary time window 234 is chosen to be one day, then the primary adherence value 232 for a corresponding primary time window will be one of four values: 0 (all three meal events of that day were regimen nonadherent), 1/3 (one of the three meal events of that day was regimen nonadherent, and the other two were regimen adherent), 2/3 (two of the three meal events of that day were regimen nonadherent, and the other one was regimen adherent), 3/3 (all three meal events of that day were regimen adherent). That is, the computed primary adherence value for the primary time window will be a number that ranges between zero and one. This primary adherence value can be multiplied by the total number of metabolic events in the primary time window to obtain 3*0 (all three meal events of that day were regimen nonadherent), 3*1/3 (one of the three meal events of that day was regimen nonadherent, and the other two were regimen adherent), 3*2/3 (two of the three meal events of that day were regimen nonadherent, and the other one was regimen adherent), 3*3/3 (all three meal events of that day were regimen adherent). In this instance, the computed primary adherence value for the primary time window will be a number that ranges between zero and three. If, on the other hand, the primary window is chosen to be a week, then the primary adherence value 232 will be one of 22 values (that range between zero and one (before multiplication against total metabolic events or some other scalar).

In some embodiments, no bolus for a particular meal is required by the bolus insulin medicament dosage regimen and thus that meal is adherent even though there was no bolus prior to the meal. For instance, some bolus regimens only assume a bolus for dinner and not for breakfast and lunch. Therefore a detected lunch meal event but no corresponding bolus would be classified as in adherence.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIG. 1, 2, or 3 and/or described in FIG. 4. These program modules can be stored on a CD-ROM, DVD, magnetic disk storage product, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

The invention claimed is:

1. A device for monitoring adherence to a prescribed insulin medicament dosage regimen for a subject over time, wherein the device comprises one or more processors and a memory, the memory storing instructions that, when executed by the one or more processors, perform a method of:
    obtaining a first data set, the first data set comprising a plurality of metabolic events the subject engaged in, wherein the plurality of metabolic events is within a first period of time and each respective metabolic event in the plurality of metabolic events comprises (i) a timestamp of the respective metabolic event and (ii) a first characterization that is one of insulin regimen adherent and insulin regimen nonadherent,
    computing a plurality of primary adherence values wherein
        each respective primary adherence value in the plurality of primary adherence values represents a corresponding primary time window in a plurality of primary time windows within the first period of time, each primary time window is of a same first fixed duration, and
        each respective primary adherence value in the plurality of primary adherence values is computed by dividing a number of insulin regimen adherent metabolic events by a total number of metabolic events in the plurality of metabolic events that have timestamps in the primary time window corresponding to the respective primary adherence value;
    identifying a trend in adherence to the prescribed insulin medicament dosage regimen for the subject as a drop off in the plurality of primary adherence values or the plurality of secondary adherence values below a first threshold adherence value for at least a second threshold amount of time;
    reducing amounts of insulin medicament dosage in the insulin medicament dosage regimen for the subject when the trend is identified; and
    communicating the plurality of primary adherence values across the first period of time thereby monitoring adherence to the prescribed insulin medicament dosage regimen for the subject over time.

2. The device of claim 1, the method further comprising: computing a plurality of secondary adherence values, wherein
    each respective secondary adherence value in the plurality of secondary adherence values represents a corresponding secondary time window in a plurality of contemporaneously overlapping secondary time windows within the first period of time,
    each respective secondary adherence value in the plurality of secondary adherence values is computed by dividing a number of metabolic events that are insulin regimen adherent by a total number of metabolic events in the plurality of metabolic events that have timestamps in the secondary time window corresponding to the respective secondary adherence value, and
    each secondary time window in at least a subset of the secondary time windows in the plurality of secondary time windows is of longer duration than the first fixed duration; and wherein the communicating comprises communicating a superposition of the plurality of primary adherence values and the plurality of secondary adherence values across the first period of time.

3. The device of claim 1, wherein each metabolic event in the plurality of metabolic events is a fasting event and the insulin medicament dosage regimen is a basal insulin medicament dosage regimen.

4. The device of claim 3, wherein
the first fixed duration is a week, and
each respective secondary time window in the plurality of secondary time windows represents three months in the first time period.

5. The device of claim 1, wherein each metabolic event in the plurality of metabolic events is a meal event and the insulin medicament dosage regimen is a bolus insulin medicament dosage regimen.

6. The device of claim 4, wherein
the first fixed duration is a day, and
each respective secondary time window in the plurality of secondary time windows represents a running average from the beginning of the first time period.

7. The device of claim 1, the method further comprising:
obtaining an HbA1c lookup table that includes a calculated HbA1c increase as a function of adherence values in the plurality of primary adherence values; and
communicating an indication of which respective primary adherence values in the plurality of primary adherence values cause the calculated HbA1c increase to be over a threshold value according to the HbA1c lookup table.

8. The device of claim 2, wherein each secondary time window is of a same second fixed duration that is greater than the first fixed duration.

9. The device of claim 1, wherein respective metabolic events in the plurality of metabolic events that occur earlier than a set cutoff time are down-weighted relative to respective metabolic events in the plurality of metabolic events that occur after the set cutoff time in each respective primary time window.

10. The device of claim 1, wherein respective metabolic events in the plurality of metabolic events are down-weighted as a linear function of time in each respective primary time window.

11. The device of claim 1, wherein the device is a mobile device that includes a display and the communicating includes presenting the superposition on the display.

12. The device of claim 1, the method further comprising:
obtaining a second data set, the second data set comprising a plurality of autonomous glucose measurements of the subject and, for each respective autonomous glucose measurement in the plurality of autonomous glucose measurements, a glucose measurement timestamp representing when the respective measurement was made; and
the communicating provides the plurality of autonomous glucose measurements temporally matched to the plurality of primary adherence values over time within the first period of time.

13. The device of claim 12, the device further comprising a wireless receiver and wherein the second data set is obtained wirelessly from a glucose sensor affixed to the subject.

14. A method of monitoring adherence to a prescribed insulin medicament dosage regimen for a subject over time, the method comprising:
obtaining a first data set the first data set comprising a plurality of metabolic events the subject engaged in, wherein the plurality of metabolic events are within a first period of time and each respective metabolic event in the plurality of metabolic events comprises (i) a timestamp of the respective metabolic event and (ii) a first characterization that is one of insulin regimen adherent and insulin regimen nonadherent,
computing a plurality of primary adherence values wherein
each respective primary adherence value in the plurality of primary adherence values represents a corresponding primary time window in a plurality of primary time windows within the first period of time,
each primary time window is of a same first fixed duration, and
each respective primary adherence value in the plurality of primary adherence values is computed by dividing a number of insulin regimen adherent metabolic events that have timestamps in the primary time window corresponding to the respective primary adherence value by a total number of metabolic events in the plurality of metabolic events that have timestamps in the primary time window corresponding to the respective primary adherence value; and
identifying a trend in adherence to the prescribed insulin medicament dosage regimen for the subject as a drop off in the plurality of primary adherence values or the plurality of secondary adherence values below a first threshold adherence value for at least a second threshold amount of time;
reducing amounts of insulin medicament dosage in the insulin medicament dosage regimen for the subject when the trend is identified; and
communicating the plurality of primary adherence values across the first period of time thereby monitoring adherence to the prescribed insulin medicament dosage regimen for the subject over time.

* * * * *